(12) United States Patent
Xu et al.

(10) Patent No.: US 9,535,016 B2
(45) Date of Patent: Jan. 3, 2017

(54) COMPTON COINCIDENT VOLUMETRIC IMAGING

(71) Applicant: William Beaumont Hospital, Royal Oak, MI (US)

(72) Inventors: Xiaochao Xu, Berkley, MI (US); Di Yan, Auburn Hills, MI (US)

( * ) Notice: Subject to any disclaimer, the term of this patent is extended or adjusted under 35 U.S.C. 154(b) by 236 days.

(21) Appl. No.: 14/194,230

(22) Filed: Feb. 28, 2014

(65) Prior Publication Data

US 2014/0241505 A1   Aug. 28, 2014

Related U.S. Application Data

(60) Provisional application No. 61/770,792, filed on Feb. 28, 2013.

(51) Int. Cl.
| | |
|---|---|
| G01N 23/201 | (2006.01) |
| G01N 23/04 | (2006.01) |
| G01N 23/20 | (2006.01) |
| A61B 6/00 | (2006.01) |

(52) U.S. Cl.
CPC ............ *G01N 23/046* (2013.01); *A61B 6/466* (2013.01); *A61B 6/5205* (2013.01); *G01N 23/20066* (2013.01); *G01N 2223/419* (2013.01)

(58) Field of Classification Search
CPC ........ G01N 23/00; G01N 23/02; G01N 23/04; G01N 23/043; G01N 23/046; G01N 23/06; G01N 23/063; G01N 23/08; G01N 23/087; G01N 2223/00

USPC .. 387/87, 21, 24, 25, 26, 27, 41, 42, 44, 46, 387/62, 64, 70
See application file for complete search history.

(56) References Cited

U.S. PATENT DOCUMENTS

| | | |
|---|---|---|
| 4,149,081 A | 4/1979 | Seppi |
| 4,598,415 A | 7/1986 | Luccio et al. |
| 4,671,102 A | 6/1987 | Vinegar et al. |
| 4,675,890 A | 6/1987 | Plessis et al. |
| 5,430,787 A | 7/1995 | Norton |
| 5,600,303 A | 2/1997 | Husseiny et al. |

(Continued)

FOREIGN PATENT DOCUMENTS

| | | |
|---|---|---|
| EP | 105032 A2 | 4/1984 |
| EP | 206372 B1 | 12/1986 |

(Continued)

OTHER PUBLICATIONS

Brooks, R. A. et al. "Statistical limitations in x-ray reconstructive tomography." Medical physics 3 (4), 237-240 (1976).

(Continued)

*Primary Examiner* — Jason McCormack

(57) ABSTRACT

A volumetric imaging device for constructing a three dimensional image includes a source, and absorbing detector, and an image constructor. The source includes a photon source, and a scatter detector arranged between the object and the photon source. The photon source emits photons towards the scatter detector. The scatter detector scatters at least some of the photons and detects the scattered photons. The object scatters at least some of the photons that were first scattered by the scatter detector. The absorbing detector is arranged to detect scattered photons from the object. The image constructor constructs the three dimensional image based on the scattered photons.

46 Claims, 17 Drawing Sheets

(56) References Cited

U.S. PATENT DOCUMENTS

| | | | |
|---|---|---|---|
| 5,692,029 A | 11/1997 | Husseiny et al. | |
| 5,861,627 A * | 1/1999 | Basko | G06T 1/1642 250/363.04 |
| 6,224,848 B1 | 5/2001 | Mills | |
| 6,359,963 B1 | 3/2002 | Cash | |
| 6,560,312 B2 | 5/2003 | Cash | |
| 6,665,373 B1 * | 12/2003 | Kotowski | G01N 23/20 378/57 |
| 7,317,192 B2 | 1/2008 | Ma | |
| 7,623,625 B2 | 11/2009 | Boyden et al. | |
| 7,627,085 B2 | 12/2009 | Boyden et al. | |
| 7,652,259 B2 | 1/2010 | Kimchy et al. | |
| 7,711,089 B2 | 5/2010 | Boyden et al. | |
| 7,724,865 B2 | 5/2010 | Wu et al. | |
| 7,724,871 B2 | 5/2010 | Boyden et al. | |
| 7,734,012 B2 | 6/2010 | Boyden et al. | |
| 7,742,564 B2 | 6/2010 | Parham et al. | |
| 7,742,567 B2 | 6/2010 | Boyden et al. | |
| 7,760,848 B2 | 7/2010 | DeMan et al. | |
| 7,885,372 B2 | 2/2011 | Edic et al. | |
| 7,931,784 B2 | 4/2011 | Medoff | |
| 8,041,006 B2 | 10/2011 | Boyden et al. | |
| 8,063,379 B2 | 11/2011 | Suhami | |
| 8,094,783 B2 | 1/2012 | Harding | |
| 8,164,074 B2 | 4/2012 | Boyden et al. | |
| 8,168,958 B2 | 5/2012 | Boyden et al. | |
| 8,203,120 B2 | 6/2012 | Zewail | |
| 8,227,204 B2 | 7/2012 | Boyden et al. | |
| 8,311,182 B2 | 11/2012 | Chandra et al. | |
| 8,315,352 B2 | 11/2012 | Wu et al. | |
| 8,363,917 B2 | 1/2013 | Fan et al. | |
| 8,454,803 B2 | 6/2013 | Medoff | |
| 8,529,426 B2 | 9/2013 | Boyden et al. | |
| 8,837,677 B2 | 9/2014 | Boyden et al. | |
| 2002/0051751 A1 | 5/2002 | Mills | |
| 2004/0136492 A1 * | 7/2004 | Sokolov | G01N 23/046 378/19 |
| 2006/0056590 A1 * | 3/2006 | Nikulin | G01N 23/083 378/71 |
| 2008/0253520 A1 | 10/2008 | Boyden et al. | |
| 2008/0253521 A1 | 10/2008 | Boyden et al. | |
| 2008/0253522 A1 | 10/2008 | Boyden et al. | |
| 2008/0253525 A1 | 10/2008 | Boyden et al. | |
| 2008/0253526 A1 | 10/2008 | Boyden et al. | |
| 2008/0253527 A1 | 10/2008 | Boyden et al. | |
| 2008/0253529 A1 | 10/2008 | Boyden et al. | |
| 2008/0253627 A1 | 10/2008 | Boyden et al. | |
| 2008/0279330 A1 * | 11/2008 | Ueki | A61B 5/0091 378/63 |
| 2009/0080597 A1 | 3/2009 | Basu | |
| 2009/0101841 A1 | 4/2009 | Boyden et al. | |
| 2009/0101875 A1 | 4/2009 | Boyden et al. | |
| 2009/0104113 A1 | 4/2009 | Boyden et al. | |
| 2010/0108567 A1 | 5/2010 | Medoff | |
| 2010/0108883 A1 | 5/2010 | Zewail | |
| 2011/0081003 A1 | 4/2011 | Harding | |
| 2011/0305318 A1 * | 12/2011 | Robinson | G01N 23/087 378/88 |
| 2012/0039438 A1 | 2/2012 | Parham et al. | |
| 2012/0039440 A1 | 2/2012 | Fan et al. | |
| 2012/0076258 A1 | 3/2012 | Chandra et al. | |
| 2012/0140887 A1 * | 6/2012 | Mundy | A61N 5/1048 378/65 |
| 2012/0157829 A1 | 6/2012 | Boyden et al. | |
| 2012/0157830 A1 | 6/2012 | Boyden et al. | |

FOREIGN PATENT DOCUMENTS

| | | |
|---|---|---|
| EP | 316440 B1 | 1/1996 |
| EP | 105032 B1 | 8/1998 |
| EP | 1980876 A2 | 10/2008 |
| EP | 1980877 A2 | 10/2008 |
| EP | 2072081 B1 | 6/2009 |
| EP | 1573495 B1 | 11/2009 |
| GB | 1594627 A | 8/1981 |
| GB | 2450773 B | 1/2009 |
| GB | 2453860 A | 4/2009 |
| WO | WO8809152 A1 | 12/1988 |
| WO | WO9841992 A1 | 9/1998 |
| WO | WO-0136997 A1 | 5/2001 |
| WO | WO2004042546 A1 | 5/2004 |
| WO | WO2004109717 A2 | 12/2004 |
| WO | WO2007087329 A2 | 8/2007 |
| WO | WO2009134745 A2 | 11/2009 |
| WO | WO2009140057 A2 | 11/2009 |
| WO | WO2010042629 A2 | 4/2010 |
| WO | WO2010065532 A2 | 6/2010 |
| WO | WO-2011011014 A1 | 1/2011 |

OTHER PUBLICATIONS

Conti, M. "State of the art and challenges of time-of-flight PET." Physica Medica 25 (1), 1-11 (2009).

Cooper, M. J. "Compton scattering and the study of electron momentum density distributions." Radiation Physics and Chemistry 50 (1), 63-76 (1997).

Evans, B. L., et al. "Demonstration of energy-coded Compton scatter tomography with fan beams for one-sided inspection." Nucl. Instr. Meth. Phys. Res. A 480, 797-806 (2002).

Gerl, J. "Gamma-ray imaging exploiting the Compton effect." Nuclear Physics A 752, 688-695 (2005).

Green, P. J. "Bayesian reconstructions from emission tomography data using a modified EM algorithm." IEEE Transactions on Medical Imaging, 9 (1), 84-93 (1990).

Gustavsson, S., et al. "Cryogenic amplifier for intermediate source impedance with gigahertz bandwidth." Applied Physics Letters 88 (15), 153505 (2006).

Guzzardi, R. et al. "A critical review of Compton imaging." Critical reviews in biomedical engineering 15 (3), 237-268 (1987).

Huda, W., et al. "Patient radiation doses from adult and pediatric CT." AJR. American Journal of Roentgenology 188, 540-546 (2007).

Hussein, Esam M. A. "On the intricacy of imaging with incoherently-scattered radiation." Nucl. Instr. Meth. Phys. Res. B 263 (1), 27-31 (2007).

Hutton, B. F. "Recent advances in iterative reconstruction for clinical SPECT/PET and CT." Acta Oncol. 50 (6), 851-858 (2011).

Kagan, H. "Recent advances in diamond detector development." Nucl. Instr. Meth. Phys. Res. A 541, 221-227 (2005).

Khettabi F. El, et al. "A nonrotating multiparameter 3-D X-ray imaging system-Part I: modeling and reconstruction." IEEE Transactions on Nuclear Science, 51 (3), 641-647 (2004).

Khettabi, F. El, et al. "A three-dimensional x-ray scattering system for multi-parameter imaging of the human head." Phys. Med. Biol. 48 (20), 3445-3458 (2003).

Knoll, G. F., [Radiation Detection and Measurement], John Wiley & Sons, Hoboken, NJ (2010) pp. 115-118, 377, 387-393.

Lale, P. G. "Examination of Internal Tissues, using Gamma-ray Scatter with a Possible Extension to Megavoltage Radiography." Phys. Med. Biol. 4 (2), 159-167 (1959).

Lalush, D. S., et al. "Iterative Image Reconstruction." Emission Tomography: The Fundamentals of PET and Spect, Academic Press, San Diego, 443-472, (2004).

Lange, K., et al. "EM reconstruction algorithms for emission and transmission tomography." Journal of Computer Assisted Tomography 8 (2), 306-316 (1984).

Lenti, M. "A 3-D imaging device using Compton scattering off the body." Nucl. Instr. Meth. Phys. Res. A 588 (3), 457-462 (2008).

Liu, Y. M., et al. "Electron Radiation Damage Effects in Silicon Surface-Barrier Detectors." IEEE Transactions on Nuclear Science, 18 (1), 192-199 (1971).

Mar, D. J., et al. "Cryogenic field-effect transistor with single electronic charge sensitivity." Applied Physics Letters 64 (5), 631-633 (1994).

Mettler, F. A., et al. "Radiologic and Nuclear Medicine Studies in the United States and Worldwide: Frequency, Radiation Dose, and Comparison with Other Radiation Sources—1950-2007." Radiology 253 (2), 520-531 (2009).

(56) References Cited

OTHER PUBLICATIONS

Moses, W. W. "Recent advances and future advances in time-of-flight PET." Nucl. Instr. Meth. Phys. Res. A 580 (2), 919-924 (2007).

Norton, S. J. "Compton scattering tomography." Journal of Applied Physics 76 (4), 2007-2015 (1994).

Pomorski, M., et al. "Development of single-crystal CVD-diamond detectors for spectroscopy and timing." Physica status solidi (a) 203 (12), 3152-3160 (2006).

Pomorski, M. "Electronic properties of single crystal CVD diamond and its suitability for particle detection in hadron physics experiments." pp. 93-137 (2008).

Shepp, L. A., et al. "Maximum Likelihood Reconstruction for Emission Tomography." IEEE Transactions on Medical Imaging, 1 (2), 113-122 (1982).

Singh, M., et al. "An electronically collimated gamma camera for single photon emission computed tomography. Part II: Image reconstruction and preliminary experimental measurements." Medical Physics 10 (4), 428-435 (1983).

Todd, R. W., et al. "A proposed γ camera." Nature 251 (5471), 132-134 (1974).

Tretiak, O. J., "Noise Limitations in X-Ray Computed Tomography." Journal of Computer Assisted Tomography 2 (4), 477-480 (1978).

Truong, T. T., et al. "Radon transforms on generalized Cormack's curves and a new Compton scatter tomography modality." Inverse Problems 27 (12), 125001 (2011).

Truong, T. T., et al. "Recent Developments on Compton Scatter Tomography: Theory and Numerical Simulations." Numerical Simulation—From Theory to Industry, InTech, Rijeka, Croatia, (2012) pp. 101-128.

Zhong, Z., et al. "Producing parallel x rays with a bent-crystal monochromator and an x-ray tube." Medical Physics 28 (9), pp. 1931-1936 (2001).

Committee to Assess Health Risks from Exposure to Low Levels of Ionizing Radiation, N. R. C., [Health Risks from Exposure to Low Levels of Ionizing Radiation: BEIR VII Phase 2], The National Academies Press, Washington, DC (2006), pp. 14-16.

\* cited by examiner

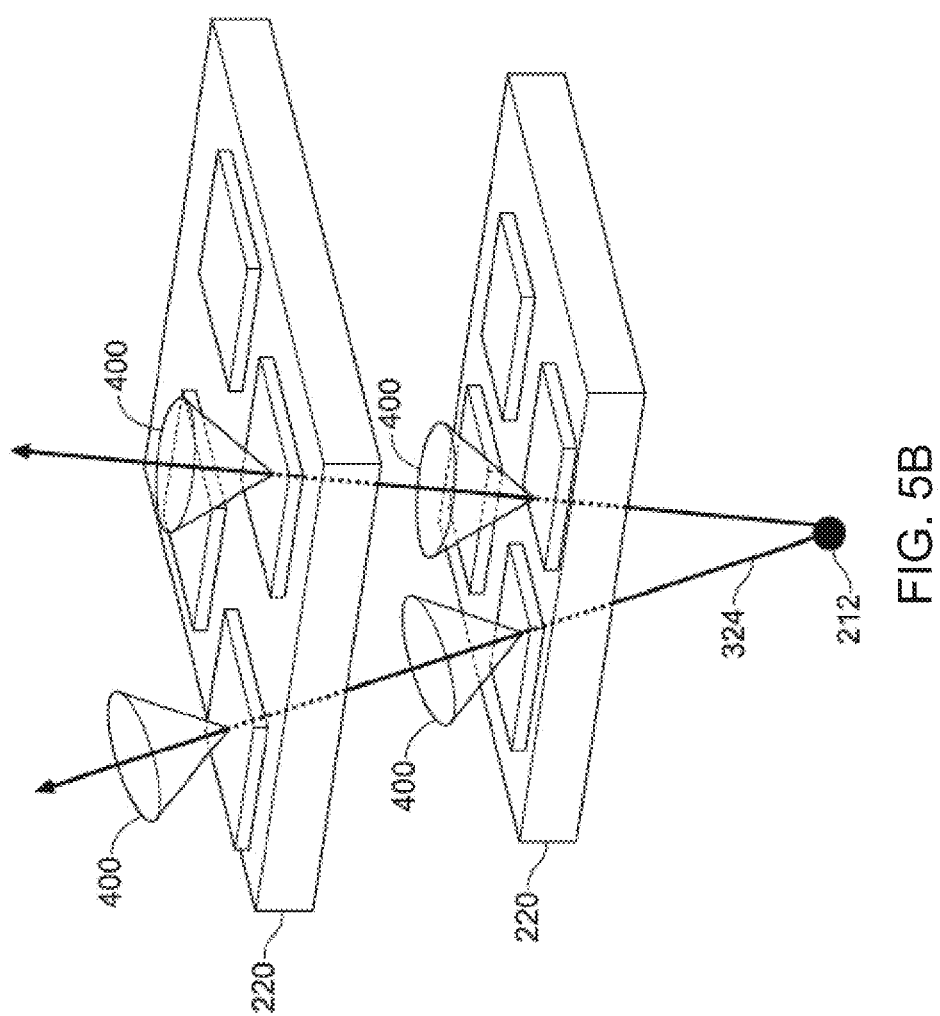

COMPTON COINCIDENT VOLUMETRIC IMAGING

TECHNICAL FIELD

This disclosure relates to three dimensional volumetric imaging using Compton Scattering.

BACKGROUND

Medical imaging refers to several different technologies used to view the human body for diagnosing, monitoring, or treating medical conditions. Several types of imaging are available, such as ultrasound imaging, magnetic resonance imaging (MRI), and x-rays. Ultrasound imaging is used for viewing soft tissues (e.g., muscles, internal organs), by emitting high-frequency sound waves. Ultrasound imaging involves placing a transducer emitting high frequency sound waves against the skin of a patient where a targeted soft tissue is observed. MRI is used for organs and internal structures of the body. MRI uses strong magnetic fields and radio waves and produces cross-sectional images of the body. The magnetic properties and water content varies between different organs and different areas of the body, therefore, distinguishing the parts from one another. MRI provides information about structure in the body that is not visible by a standard x-ray, an ultrasound, or a computed tomography (CT) exam. X-ray imaging uses radiation, high energy photons emitted through the x-ray source and traveling through the air reaching a patient. The energy of the individual photons emitted by the x-ray device is strong enough to penetrate a patient's body including body tissue and internal organs, and then onto an x-ray detector. The various body tissue and internal organs have different densities. Therefore, each organ transmits the x-ray photons differently than the other, allowing the x-ray detector to differentiate between the different parts of the body. Several types of x-ray imaging modalities are available including, but not limited to, x-ray radiography, mammography, and computed tomography (CT). Patients exposed to x-ray imaging face the risk of reacting to an intravenous contrast agent used for improving visualization of the internal body parts. In addition, risks can include an increased risk of developing cancer in a patient's lifetime. This risk is prominently determined by the organ irradiated, the sex of the patient, the age of the patient at the time of exposure, and most importantly the radiation dose, which is the amount of energy absorbed by the body.

SUMMARY

One aspect of the disclosure provides a volumetric imaging device for constructing a three dimensional image. The volumetric imaging device includes a source, an absorbing detector, and an imaging constructor. The source includes a photon source and a scatter detector. The scatter detector is arranged between the object and the photon source, and scatters at least some of the photons and records the energy of the scattered photons. The object also scatters at least some of the photons. The absorbing detector is arranged to detect the scattered photons from the object. The image constructor constructs the three dimensional image based on the scattered photons.

Implementations of the disclosure may include one or more of the following features. In some implementations, at least some of the photons emitted from the source impact an object and are further scattered by the object. The image constructor may calculate an electron density of the object.

In some examples, the scatter and the absorbing detectors detect a photon simultaneously. The scatter detector may have a thickness of about 1 mm.

In some implementations, the source further includes an electron detector positioned adjacent to the scatter detector. Additionally or alternatively, the photon source may be a synchrotron radiation source, an X-Ray tube with a monochromator, or a radioisotope (e.g., Cesium-137 with a photon energy of 662 keV). The photon beam may have a threshold value of 250 keV.

In some examples, the detectors are static with respect to one another. Additionally or alternately, the scatter detector may measure a first recoil energy $E_e$ being an energy of electrons.

In some examples, a time-of-flight is determined by recording the arrival time of the detected photons at the scatter detector and the absorbing detector. An electron detector may be positioned behind the scatter detector for detecting escaped electrons from the scatter detector.

The image constructor may receive location information of the scattered photons based on a location determined by $(\vec{r}_2, \theta_1, \theta_2)$ in a spherical coordinate system, wherein $\vec{r}_2$ is the absorbing detector pixel positions, $\theta_1$ is a scattering photon angle at the scatter detector and $\theta_2$ is a scattering photon angle at the object.

Another aspect of the disclosure provides a volumetric imaging device for capturing an image of an object. The volumetric imaging device includes a photon source that emits a beam of photons and scatter and absorbing detectors. The scatter detector is positioned between the object and the photon source and scatters and detects at least some of the photons emitted from the photon source. The scatter detector detects the scattered photons. At least some of the scattered photons impact the object and are further scattered by the object. The absorbing detector is arranged to detect photons scattered by the scatter detector and the object, the scatter and absorbing detectors simultaneously detecting a photon. The scatter detector may have a thickness of about 1 mm. The photon beam may have a threshold value of 250 keV.

In some implementations, the photon source includes an electron detector positioned adjacent to the scatter detector. The photon source may be one of a synchrotron radiation source, an X-Ray tube with a monochromator, or a radioisotope (e.g., Cesium-137 with a photon energy of 662 keV). In some examples, the detectors are static with respect to one another.

In some examples, a time-of-flight is determined by recording the arrival time of the detected photons at the scatter detector and the absorbing detector. Additionally or alternatively, an electron detector positioned behind the scatter detector detects escaped electrons from the scatter detector. In some examples, the image constructor receives location information of the scattered photons based on a location determined by $(\vec{r}_2, \theta_1, \theta_2)$ in a spherical coordinate system, wherein $\vec{r}_2$ is the absorbing detector pixel positions, $\theta_1$ is a scattering photon angle at the scatter detector and $\theta_2$ is a scattering photon angle at the object.

Another aspect of the invention provides a method of volumetric imaging of an object. The method includes emitting a photon beam from a photon source through a scatter detector and towards an object. The scatter detector scatters at least some of the photons emitted by the photon source, and detects the scattered photons. The method further includes measuring energies of photons scattered by the scatter detector, and measuring energies of photons scattered by the object. The method further includes determining a scattered angle of photons scattered by the scatter detector, and determining a scattered angle of photons scattered by the imaging object. Additionally, the method includes constructing a three-dimensional image based on the determined scattering angles and the determined scattering photon energies.

In yet another aspect of the disclosure, a method of volumetric imaging of an object is provided. The method includes emitting a photon beam from a photon source through a scatter detector towards the object. The scatter detector has electrons and scatters at least some of the photons. The method further includes measuring energies of photons scattered by the scatter detector and measuring energies of photons scattered by the object. The method also includes executing a routine on a computing processor that computes a scattering angle of photons scattered by the scatter detector and a scattering angle of photons scattered by an absorbing detector, and the routine further constructs a three dimensional image based on the computed scattering angles and the computed scattering photon energies.

In some examples, the method includes determining the scattered angle and the scattering energy of a photon scattered by the scatter and absorbing detectors occurring simultaneously. In some examples, the method further includes determining an electron density of the object. In some implementations, computing the scattering angle and the scattering energy of photons scattered by the scatter and absorbing detectors occurs simultaneously.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 5B is a perspective view of an exemplary multiple scatter detector with a point-like source beam.

Like reference symbols in the various drawings indicate like elements.

DETAILED DESCRIPTION

Compton scattering is a dominant interaction during radiography and computed tomography x-ray imaging. The Compton scattering of photons results in scattered photons the scattering of photons that are not usually used for extracting an image or image information. Therefore, it is desirable to use an imaging device (the Compton Coincidence volumetric imaging device (CCVI)) capable of utilizing the scattered photons for effectively extracting an image or imaging information.

Figure 1:
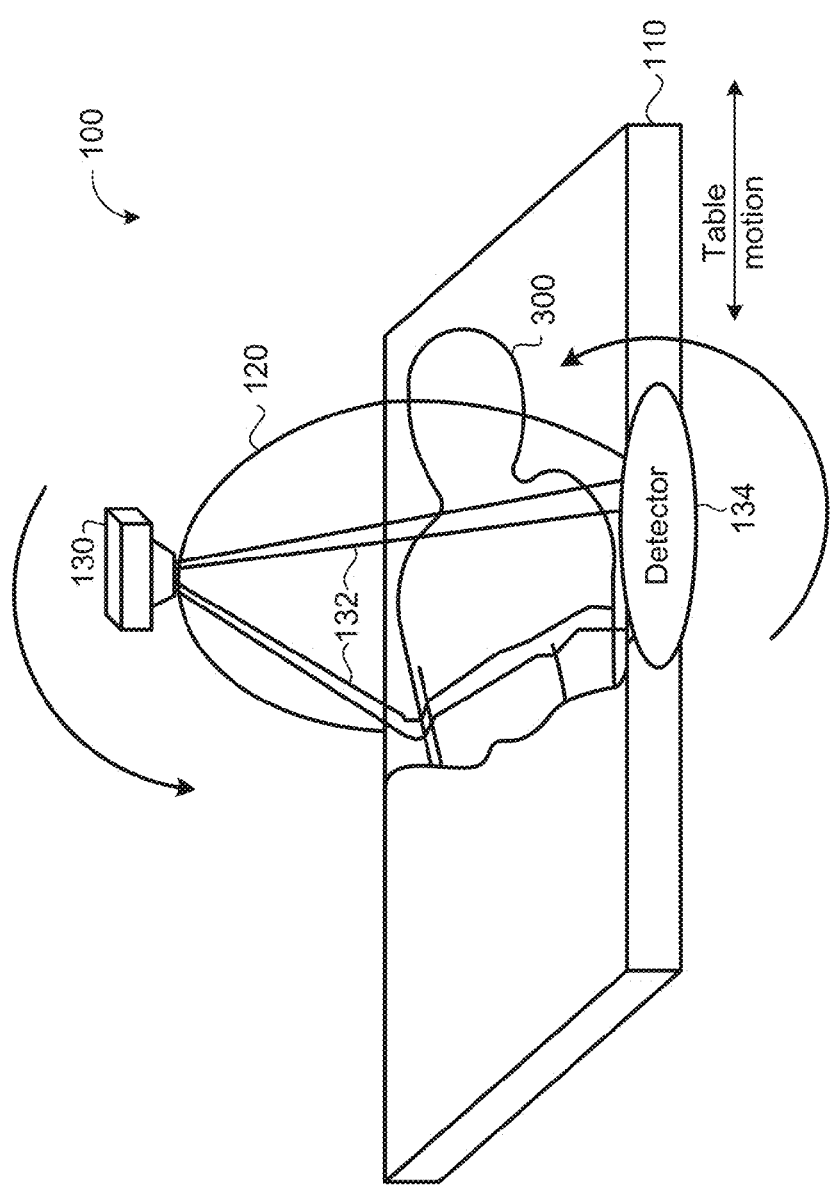
FIG. 1 is a perspective view of an imaging device.

Computed tomography (CT) imaging also known as computerized axial tomography (CAT) imaging, produces cross-sectional images or slices of parts of the body. Referring to FIG. 1, a CT system 100 includes a moving table 110 that moves in and out of a CT imaging device (not shown). An object (e.g., a patient, a patient's body, or body part) 300 is placed on the moving table 110, which moves through a circular opening 120 of the CT imaging device. CT system 100 includes an x-ray source 130 and an x-ray detector 134 placed on opposite ends of the circular opening 120 and both rotating when the CT system is activated. Once the patient 300 is within a specified distance inside the opening 120, the x-ray source 130 and the x-ray detector 134 rotate within the device about the patient 300. The x-ray source 130 emits a fan-like beam of x-rays 132 that passes through a portion of the patient's body 300. The x-ray detector 134 detects the beam of x-rays 132 that pass through the patient's body 300 as an image. Several images are collected in one rotation of the x-ray source 130 and x-ray detector 134, each taken at a different angle. The images collected are then reconstructed into one or more cross sectional images of the internal organs and/or tissues of the patient 300. CT imaging creates several risks to a patient 300 including an increased risk of cancer during the patient's lifetime due to the exposure of the x-ray radiation. In some instances, a contrast agent used to enhance visualization of the internal body parts causes an allergic reaction or may lead to kidney failure. CT and radiographic imaging utilize transmitted X-rays to form an image. The transmitted photons do not undergo any measurable interactions; therefore, they do not convey imaging information. The interacting photons are the scattered photons, which are discarded because they result in unwanted noise. When these scattered photons enter a detector, they deteriorate the image. Therefore, as described below, the CCVI device utilizes the scattered photons as part of the imaging process.

When undergoing an x-ray CT, a physician determines a patient's radiation dose (the amount of radiation the patient 300 should be exposed to) by considering the patient's age, size and location of the body part being examined, the type of procedure, and the type of equipment being used. Therefore, the radiation dose varies from patient 300 to patient 300. The effective dose is a measure of the cancer risk to a whole organism due to ionizing radiation delivered to a part of the body, which considers the type of radiation (e.g., x-ray, gamma rays, electrons (beta rays), alpha particles, neutrons, or other types of rays) and the nature of the organ. Each specific organ or body tissue has a specific weighing factor used to calculate the effective dose. The weighing factor of an organ or tissue estimates a fraction of health risk or biological effect associated with that tissue or organ. Currently, X-ray CT is the primary diagnostic imaging modality. However, as described, each scan exposes the patient 300 to cumulative radiation doses, which may potentially lead to cancer or other health problems. Therefore, it is also desirable to reduce CT imaging doses.

Figure 2A:
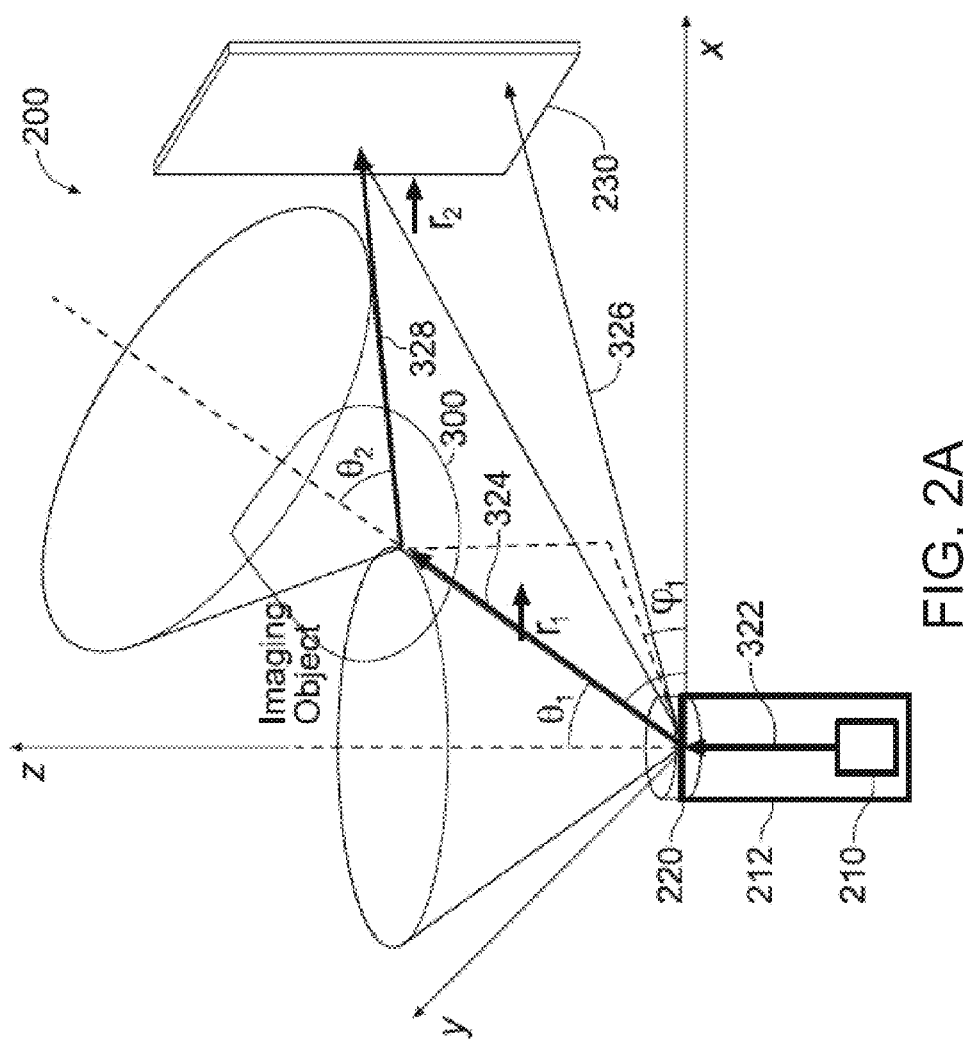
FIG. 2A is a perspective view of an exemplary Compton coincident volumetric imaging device.
Figure 2B:
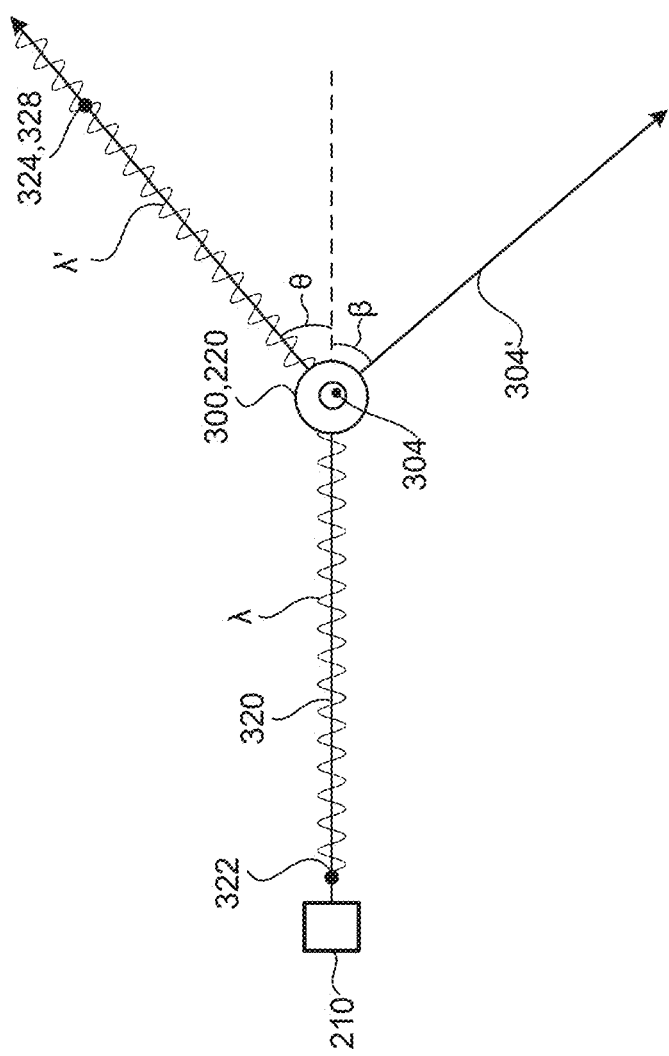
FIG. 2B is a schematic view of a Compton scattering process.

Referring to FIGS. 2A-2B, in some implementations, a Compton coincident volumetric imaging (CCVI) device 200 is provided. The CCVI device 200 utilizes Compton scattered photons for constructing an image. Unlike the CT imaging devices, the CCVI device 200 does not include a moving part that rotates about the patient 300 potentially enabling faster capturing of three dimensional volumetric images. By eliminating any moving parts, the CCVI offers a cost reduction over other imaging devices and an increase in imaging speed. In addition, the use of Compton scattering in the CCVI device 200 reduces the radiation dose a patient 300 is required to take, therefore avoiding some of the risks that the radiation dose causes. Even with the reduced dose, the resolution of the resulting images is not compromised.

In some implementations, the system utilizes an x-ray or γ-ray beam of known origin to form volumetric images of an object 300 placed between two sets of detectors 220, 230. The energy $E_0$ and direction of the source photons 322 are known and the scatter detector 220 is part of the detecting system 200 as well as the imaging source 212. Additionally, the CCVI device 200 utilizes the information of the scattered photons, 328 directly and effectively, reducing the imaging dose administered to the patient 300. Furthermore, a CCVI modality will have no moving parts, which potentially offers cost reduction and faster imaging speed.

When x-rays with a known wavelength λ interact with electrons in an object 300, the x-rays are Compton scattered at different wavelengths from their original wavelengths. The wavelengths of the Compton scattered x-rays are longer than the original wavelength, and therefore the wavelengths of the scattered x-rays have less energy than the initial wavelengths. Compton scattering (see FIG. 2B) is the scattering of x-ray photons 322 caused by the collision of the photons 322 with electrons 304. During Compton scattering, some of the energy of the photon 322 transfers to the electrons 304. The transfer of the energy of the photon 322 is more apparent for high frequency (higher energy >a few 10 s keV) x-ray photons 322 than for lower frequency photons. For lower frequency (lower energy, <a few keV) x-ray photons 322, Thomson scattering, the scattered photon 324 (imaging photons) keeps its original energy (frequency), and only changes its traveling direction. Compton scattering assumes that each scattered x-ray photon 324 interacts with only one electron 304 in a target object 300. A photon 322 having a wavelength λ is emitted from a source 210 and collides with an object 300 having an electron 304. When the photon 322 impacts the electron 304, the electron 304 recoils as a released electron 304' at an angle β and a scattered photon 324 with a wavelength λ' is released from the object 300 at an angle θ. Wavelength λ' of the scattered photon 324 is different than wavelength λ of the initial photon 322. Compton scattering considers that a photon 322 has momentum and energy, and that the energy of the incoming photon 322 is equal to the energies of the released photon 324 and the released electron 304'. Therefore, Compton scattering calculations apply the concepts of energy conservation to calculate the energies of the released photons 324 and electrons 304.

The probability of photons 320 being scattered by electrons 304 in Compton scattering is proportional to the density of the electrons 304 in the impacted object 300. Therefore, determining a spatial distribution of the scattering frequency (proportional to the probability), allows the conversion of the spatial distribution to the electron density of the material. Electron density is the number of electrons 304 in a unit volume. Electron density images are less sensitive to bone tissues as the Compton scatter cross section does not explicitly depend on the atomic number (Z value) of the different atoms in the object 300, while the photoelectric effect used in CT scans heavily depends on the atomic number of an atom. Therefore, the Compton scatter may produce a smaller contrast between bone tissues and soft tissues. In some examples, the total image contrast is the same, resulting in a better contrast between different soft tissues, which is desirable property for soft tissue imaging.

Referring to FIG. 2A, in some implementations, the CCVI device 200, includes a photon source 210 that emits a photon beam 320 of photons 322, a scatter detector 220, and an image or absorbing areal detector 230. The scatter detector 220 is positioned between the photon source 210 and the object 300. The scatter detector 220 detects and scatters some photons 322 as scattered photons 324, 326. At least some of the scattered photons 324 impact the object 300 and are further scattered by the object 300 as scattered photons 328. The image detector 230 is positioned to detect photons 328 scattered by the object 300. As further described below, the scatter detector 220 and the absorbing detector 230 simultaneously detect photons 322. The absorbing detector 230 detects scattered photons 328 scattered from the object 300 and photons scattered 326 by the scatter detector 220.

In some implementations, the photon source 210 is a collimated monochromatic x-ray or gamma ray (γ-ray) with energy $E_0$. Energy $E_0$ may be several hundred kiloelectron volts (keV) produced from a radioisotope (such as 662 keV Cs-137), a synchrotron radiation source, or an x-ray tube with a specially designed monochromator. The photons 322 in the photon beam 320 emitted from the source 210 intersect the scatter detector 220. The scatter detector 220 may be thin, e.g., about 1 mm in thickness, other thicknesses may also be possible. The scatter detector 220 is part of an imaging source 212 and detects the emitted photons 322 from the source 210. A majority of the emitted photons 322 may pass through the scatter detector 220 without being scattered. A small portion of the photons 322 in the photon beam 320 may collide with the electrons 304 in the scatter detector 220, and those colliding photons 322 may be Compton scattered by the electrons 304; some are scattered as photons 324 (which impact the object 300), some photons 326 impact the image detector 230 without being scattered by the object 300 (they can either impact the object 300 or not impacte 300), and some photons impact neither the object 300 nor the image detector 230.

In some examples, and due to the thinness of the scatter detector 220, a negligible amount of multiple scattering may occur. A scattering event may be single scattering or multiple scattering. Single scattering occurs when the emitted source photon 322 is scattered by only one localized scattering center, while multiple scattering occurs when the emitted photons 322 a first time and scatters at least one more time within the scatter detector 220. In rare occasions, multi-scattering occurs in the scatter detector 220, but because such an occurrence is rare, it does not affect the CCVI device 200 imaging and may be ignored in most cases.

When a photon 322 collides with a scatter detector 220 (or an object 300) having electrons 304, the colliding photon 322 and electron 304 transfer energies to a released photon 324 and a released electron 304', therefore conserving energies. Applying the principles of energy conservation, the summation of the energy $E_0$ of an emitted photon 322 and the kinetic energy $E_s$, of an electron 304 equals the summation of the energy $E_e$ of a recoil electron 304 and the energy of the escaped photon $E_1$, as shown in equation 1.

$$E_0 + E_s = E_1 + E_e \quad (1)$$

The kinetic energy $E_s$, of the electron 304 is negligibly small compared to the energy of the emitted photon $E_0$. Thus, equation 1 may be simplified to:

$$E_0 = E_1 + E_e \quad (2)$$

Additionally, equation 2 may be rewritten as:

$$E_1 = E_0 - E_e \quad (3)$$

The scattered photon 324 energy $E_1$ and scattering angle $\theta_1$ may be calculated from the measurement of the energy $E_e$ of the recoil electron 304' through the following equation:

$$\frac{1}{E_1} = \frac{1}{E_0} + \frac{1}{m_e}(1 - \cos(\theta_1)); \quad (4)$$

where $m_e$ is the electron mass and equals 511 keV.

Some of the Compton scattered photons 324 from the scatter detector 220 with angle $\theta_1$ travel to the object 300 to be imaged (e.g., patient). When a scattered photon 324 hits the object 300, a second Compton scattering event may occur. (The first Compton scattering event occurred at the scatter detector 220 and resulted in scattered photons 324, 326.) Thus, some of the photons 324 that hit the object 300 are Compton scattered again (by the electrons 304 in the object 300) as photons 328. The photons 328 that were scattered by the object 300 and the photons that were not scattered by the object 300 (i.e., the scattered photons 326 that were scattered once by the detector 220) are both detected and recorded by an absorbing detector 230. The absorbing detector 230 is positioned around the object 300 (FIG. 2A), i.e., the absorbing detector 230 surrounds the object 300 to detect more scattered photons 326, 328, which reduces the dose and increases the imaging speed. Additionally, the absorbing detector 230 may be an areal detector. Considering the recorded energies of the photons 322 before and photons 328 after the scattering event (by the object 300), the scattering angle $\theta_2$ of the scattered photons 328 by the object 300 (e.g., patient 300) can be calculated using equations 1-4.

In some examples, a simulated CCVI device 200 includes an object 300 having a concentric sphere with a 1-cm diameter inner sphere having an electron density of water ($3.33 \times 10^{23}$ cm$^{-3}$) surrounded by a shell having an electron density of aluminum ($7.83 \times 10^{23}$ cm$^{-3}$). The inner and outer diameters of this shell are 1 and 2 cm, respectively. The sphere's center is placed at (2, 0, 0) cm. The absorbing detector 220, assumed to have ideal detector pixels, is placed on the plane x=4 cm and is centered at (4, 0, 0) cm. The detector size is 8×8 cm$^2$, divided into 64×64 pixels. The imaging events may be generated using Monte Carlo simulation codes, which are computational algorithms that rely on repeated random samplings to obtain numerical results. A simulated monoenergetic source 210 emits photons 322 having energy equaling 250 keV. Only Compton scattering events are generated and other effects are not considered since Compton scattering dominates over other effects. In this case, multiple scattering occurs more frequently for objects 300 having a size comparable to the mean free path of the photons 322. The mean free path of the photons 322 is the average distance travelled by a moving particle between a first location and a second location, where the second location modifies the photon's direction or energy or other particle properties.

Figure 3A:
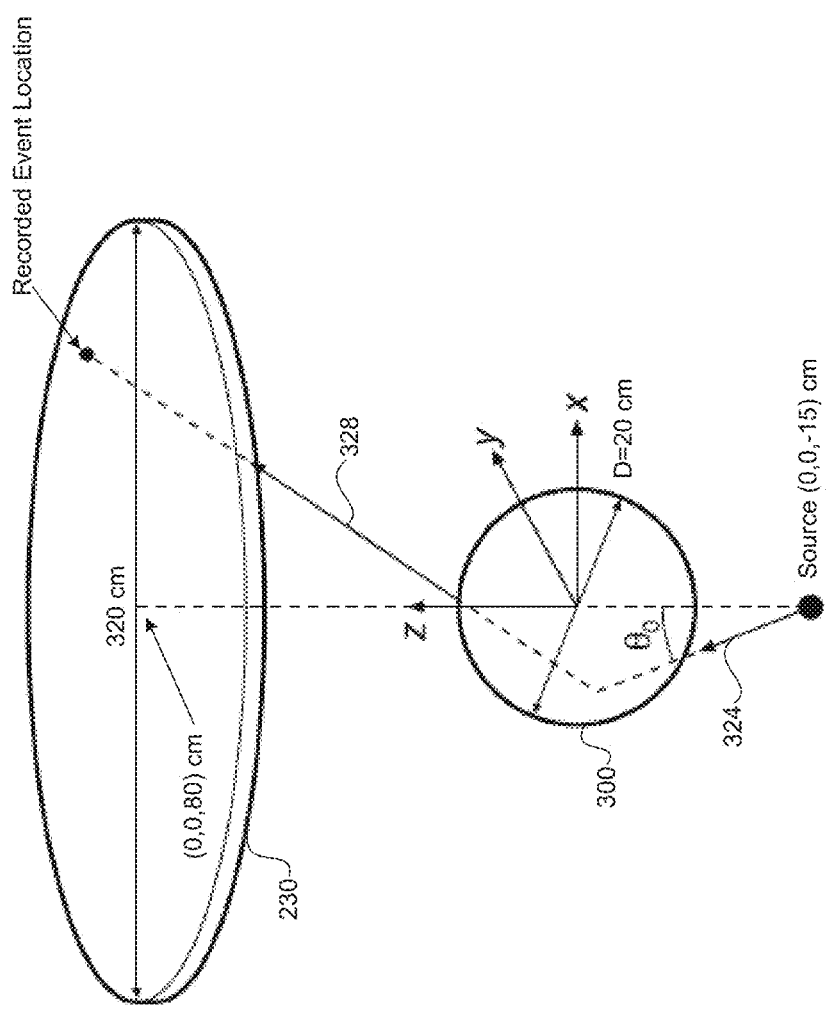
FIG. 3A is a schematic view of a simulation of multiple scatter photon rejection.

Referring to FIG. 3A, considering the previous example on a larger scale, the simulation geometry uses a monoergentic point source of 250 keV. The setup is circularly symmetric along the z-axis. This symmetry simplifies the visualization of the results (an angular average can be taken, so the data can be displayed in a 3D plot). Once again a Monte Carlo simulation is applied, varying the cone angle $\theta_0$. The simulated photons 322 are scattered in the sphere 300 (i.e., object) up to five times. After passing the sphere 300, scattered or unscattered photons 324 exit the sphere as photon 328 if scattered and are detected by an ideal areal detector 230.

Referring back to FIG. 2A, the scatter detector 220 and the absorbing detector 230 work in coincident mode, which means that the two detectors 220, 230 detect a signal of certain energies simultaneously. Since the photons 324, 326 from the scatter detector 220 travel at the speed of light to the absorbing detector 230, such simultaneous detection is possible, especially due to the scale of the CCVI device 200. In some examples, when the photons 324, 326 are not simultaneously detected, the photons 324, 326 may be considered as noise, a stray event, a non-scattered event, or a multiple scattering event. Eliminating these unwanted events greatly enhances the quality of the constructed image.

Figure 3B:
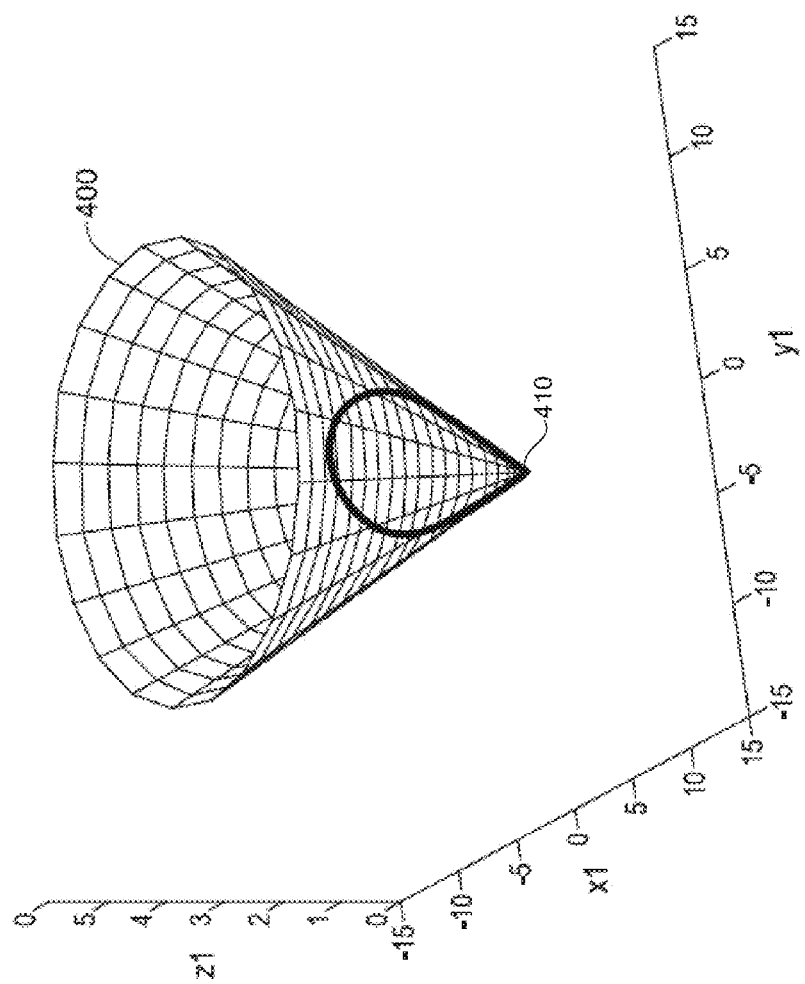
FIG. 3B is a graphical representation of a three dimensional curve showing the possible positions of $\vec{r}_1$ of FIG. 2A on a cone surface with cone angle of $\theta_1$.

Referring to FIGS. 2A and 3B, CCVI device 200 captures the electron density of an object 300 and forms a volumetric image of the object 300. The volumetric image of the object 300 is constructed using the location of the scattered photons 324, 328 scattered by the scatter detector 220 at $\vec{r_1}$ and the location of the scattered photons 328 by the object 300 at $\vec{r_2}$. We can determine the scatter event location $\vec{r_1}$ using the following equation:

$$\frac{\vec{r_1} \cdot (\vec{r_2} - \vec{r_1})}{|\vec{r_1}||\vec{r_2} - \vec{r_1}|} = \cos(\theta_2) \quad (5)$$

where $\vec{r_2}$ is the absorbing detector 230 pixel position. Equation 5 forms a curve located on a Compton scattering cone surface 400 having an origin 410 at the scatter detector 220 with cone angle $2\theta_1$ (FIG. 3B). The electron density on different cones with different cone angle $\theta_1$ is measured simultaneously without any mechanical scanning and can be reconstructed in parallel as well, enabling fast measurement and reconstruction. The final volumetric image can be reconstructed from the values of different cone surfaces by interpolation.

In some implementations, the scatter detector 220 is a thin (around 1 mm) silicon detector. Additionally or alternatively, other types of detectors may be used. The detected signals are generated by the recoiled electrons 304 after the electrons 304 scatter the incoming monoenergetic photons 322. The acquired kinetic energies by the electrons 304', which may be detected by the scatter detector 220, are of the order of tens keV to hundreds keV, determined by the Compton scatter equation 4 (see above). Most of the recoil electrons 304' do not escape the scatter detector 220 because of a low penetrating power of the electrons 304. A continuous-slowing-down-approximation (CSDA) range is an approximation of an average distance covered by a particle having a charge. As the charged particle travels a distance, it loses energy at every point along its path. Therefore, CSDA assumes that the rate of energy loss along a traveled path of a charged particle is equal to the total stopping power of the particle. The total stopping power of a particle is an average energy loss of the particle per unit length of the path. The total stopping power may be measured in Mev/cm.

Figure 4:
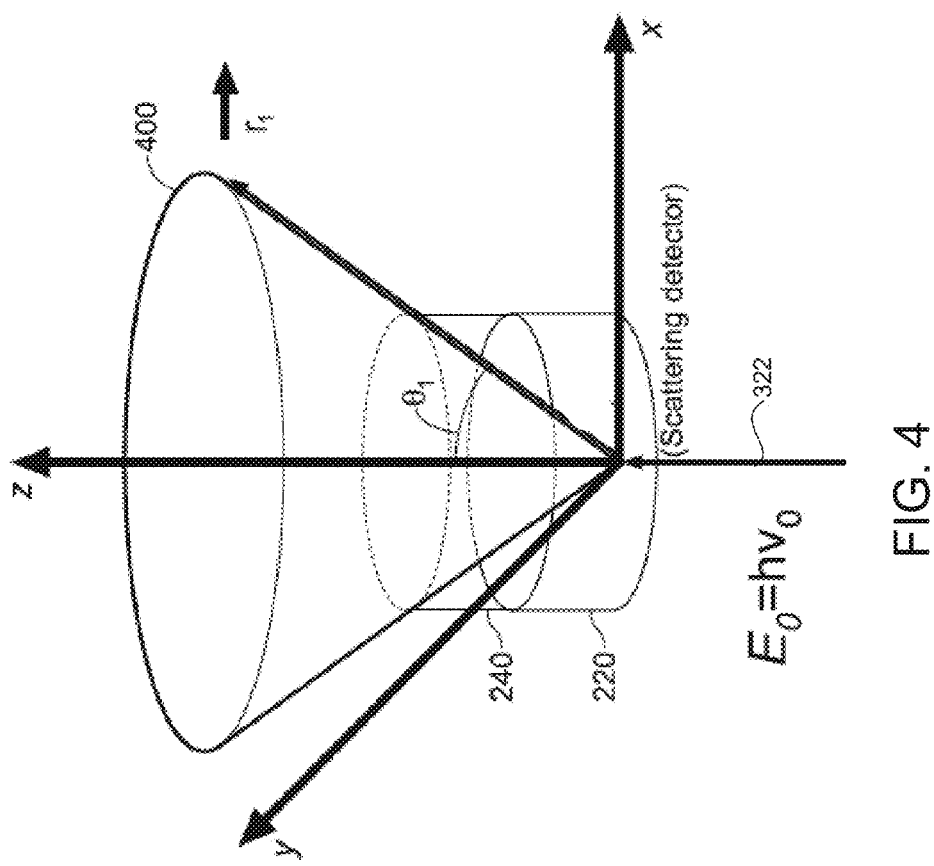
FIG. 4 is a schematic view of an exemplary Compton coincident volumetric imaging device having two detectors at the source.

Referring to FIG. 4, in some examples, at 100 keV, the CSDA range of electrons 304 in silicon is about 71 µm (this is very short compared with the 1 mm thickness of the silicon detector). However, a small portion of the electrons 304 may escape the detector 220. The escaped electrons 304 generate erroneous readings if they deposit part of their kinetic energy in the scatter detector 220. In order to eliminate these erroneous events, a thin silicon detector or an electron detector 240 is isolated behind the scatter detector 220 and is in close proximity with the scatter detector 220. Thus the escaped electrons 304' may be detected by the electron detector 240. The electron detector 240 also works in coincident mode with the scatter detector 220. If the scatter detector 220 and the electron detector 240 detect a coincident event, the event is regarded as an escaped electron event and is discarded. Other types of detectors 240 may also be used.

The scatter detector 220 is illuminated with a collimated and strong x-ray radiation 320 when the source 210 emits its photons 322. The emitted photons 322 may damage the scatter detector 220. In some examples, a photon energy threshold is used. When the photon energy is below the photon energy threshold, the silicon crystal of the scatter detector 220 suffers very little or negligible damage from the photons 322 emitted by the source 210. The energy threshold may be about 250 keV to avoid damaging the scatter detector 220. Additionally, if the photoelectric interaction between the photons 322 and the scatter detector 220 can be ignored, the threshold may be 410 keV due to the fact that the maximum recoil energy $E_e$ acquired by the recoil electron 304' is less than the incoming photon energy $E_0$ (Eq. 1).

In some implementations, a diamond detector is considered as the scatter detector 220 since the use of higher-energy imaging photons 322 improve the image resolution but cause radiation damage. The diamond detector has a higher tolerance for a higher radiation threshold than the silicon detector 220, and in some instances is faster than a silicon detector 220.

Time-of-flight (TOF) is the time it takes for an object or a particle to travel a distance through a medium. Additionally or alternatively, CCVI device 200 may detect the TOF of the photons 322, 326, 328 at the two detectors 220, 230 and reconstruct an image based on the TOF. The use of TOF for image reconstruction provides a precise calculation of the scattering event. Because multi-scattered photons travel a longer path since they are scattered more than once within the object 300, (if both a single-scattered photons and a multi-scattered photons are detected by the same imaging pixel with the same energy), TOF may be used to distinguish the multi-scattered event from the single scattered event.

In some implementations, the CCVI device 200 forms two dimensional images of the object 300. In these 2D images, the inner structures (e.g., body organs) overlay each other. This is to simulate the ordinary radiographic images. In some examples, a linear collimator with a variable width for blocking radiation to organs that are not imaged is used. Since a two dimensional image is being reconstructed instead of a three dimensional image, the patient 300 may be administered a reduced dose.

Figure 5A:
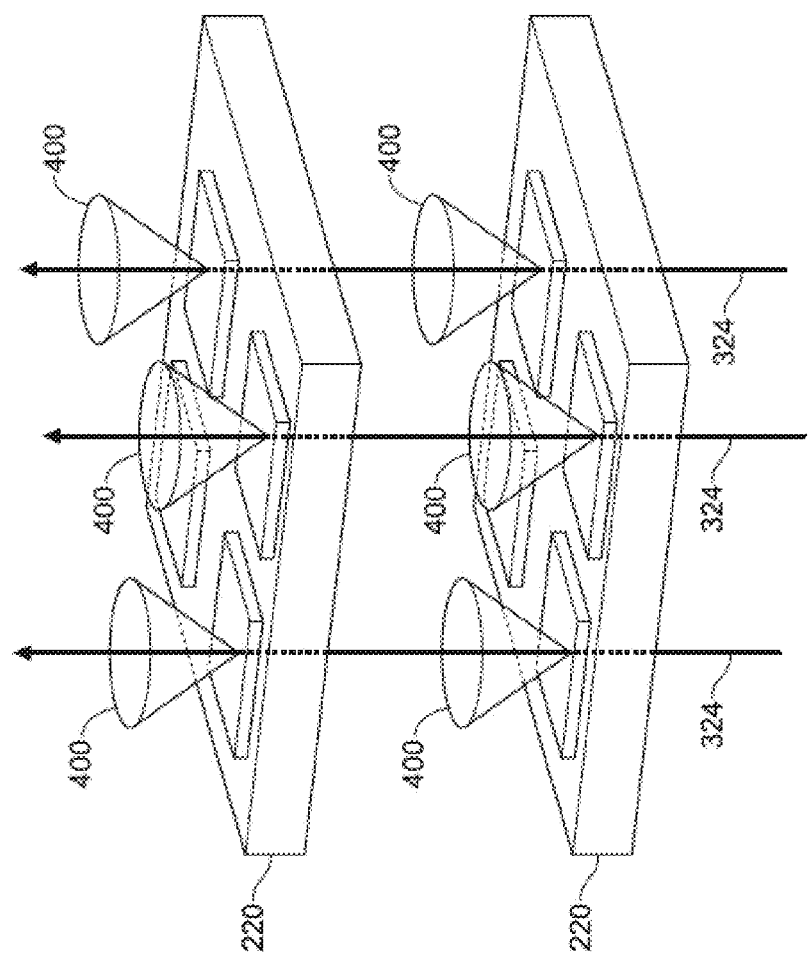
FIG. 5A is a perspective view of an exemplary multiple scatter detector with a parallel source beam.

Referring to FIGS. 5A and 5B, in some implementations, more than one scatter detector 220 may be used. The multiple scatter detectors 220 may be positioned side-by-side and/or stacked one on top of another. The time required to capture an image of an object 300 is important; therefore, to shorten the required time, multiple scatter detectors 220 may be used. The scatter detectors 220 may be arranged in series to take advantage of the transmitted photons 322. The detection of the photons 322 works in parallel, thus speeding up the imaging process. In some examples, multiple detectors 220 may be arranged in parallel.

There is a great advantage in manufacturing these detectors 220 in side-by-side as they can be made on one single silicon wafer without the need for manufacturing them separately; and the manufacturing process is the standard semiconductor processing, which is widely available due to the development of semiconductor industry. The photon source for multiple detectors 220 on one wafer can be collimated onto the individual detectors 220. One thick beam 324 can be used if the gap between the side-by-side detectors 220 is small and measures are taken to make sure the beam is well-collimated (FIG. 5A). Alternatively, a small point-like source 212 can be used (FIG. 5B).

With multiple scatter detectors 220 in parallel and series, the ultimate limiting factor of the imaging speed is the time resolution of the coincidence detection. If 10% of these photons 322 are single Compton scattered by the object 300, $10^6$ voxels (100×100×100) are imaged and each voxel scatters 4000 photons 322 on average (as in the example discussed in the dose discussion, average resolution 2 mm), these parameters yield a total imaging time of about 40 seconds.

Figure 6A:
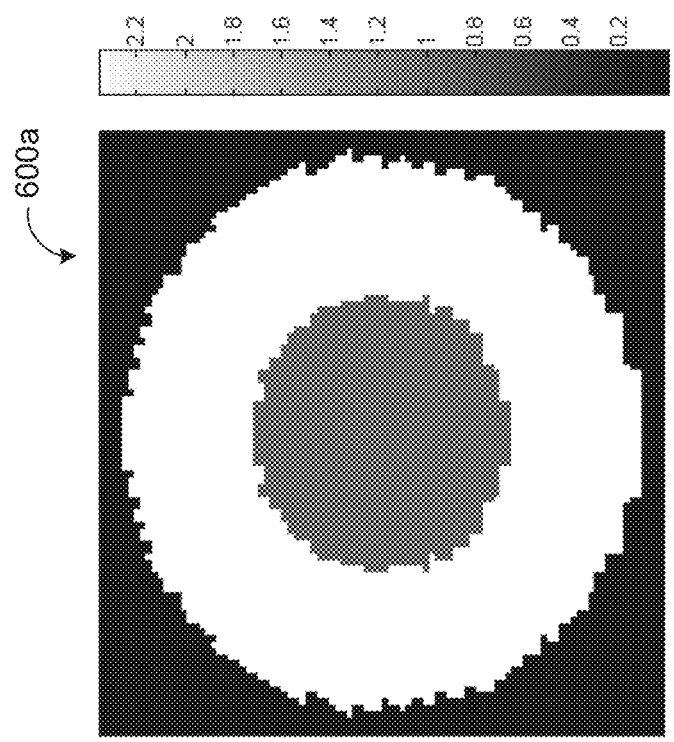
FIG. 6A is an exemplary top view of a slice of a spherical phantom.
Figure 6B:
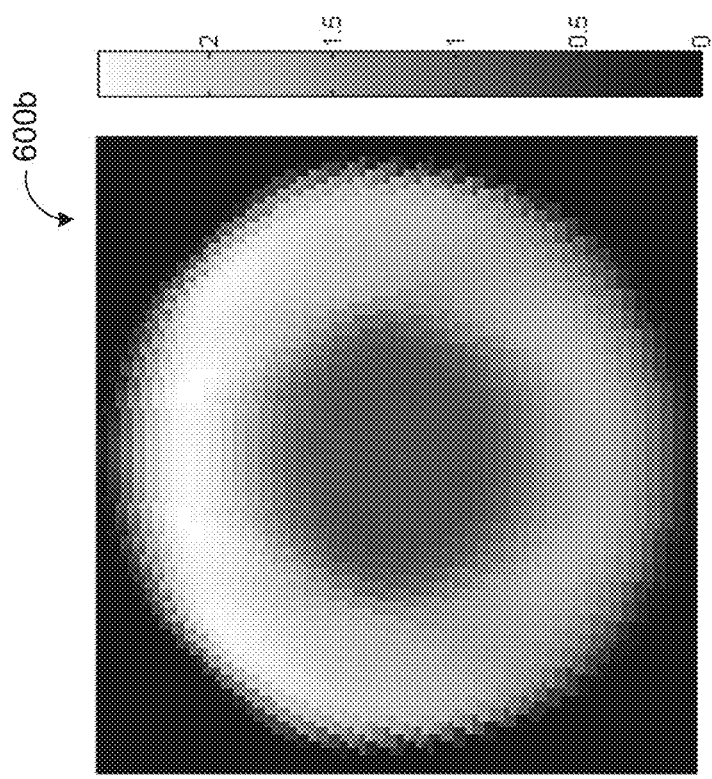
FIG. 6B is an exemplary top view of a reconstructed Compton scattering frequency map of the slice is FIG. 6A.
Figure 6C:
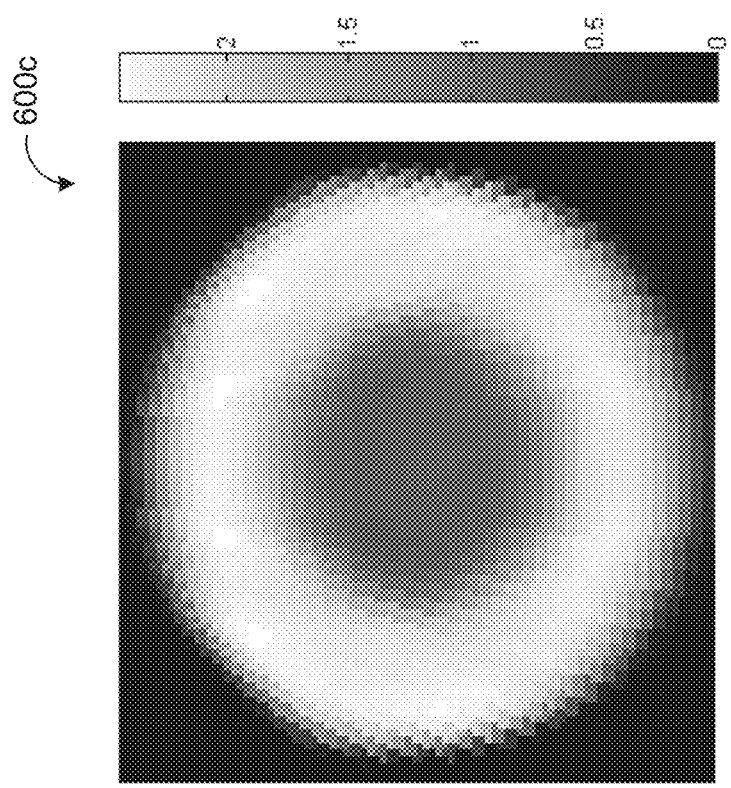
FIG. 6C is an exemplary top view of a reconstructed slice after attenuation correction.

Referring to FIGS. 6A, 6B, and 6C, in some examples, statistical iterative image reconstruction is used to reconstruct captured data into an image. Statistical iterative imaging reconstruction has been the standard for PET and SPECT image reconstruction. Various statistical iterative imaging reconstruction algorithms have been developed and they can be used directly. The major difference from those used in PET and SPECT reconstruction is the system matrix. The system matrix models the physical process of imaging previously described. The following is the procedure used to reconstruct the images in CCVI device 200:

1) The 3D CCVI image is subdivided into many 2D reconstruction sections on the cone surfaces 400 with different $\theta_1$'s whose origins are at the scatter detector 220. The construction on the cone surfaces 400 are performed separately; and in some examples, the construction of the cone can be performed in parallel to accelerate the image reconstruction process. The cone surfaces 400 have non-uniform thickness, but cover a uniform polar angle $\Delta\theta_1$. In addition, the natural coordinate system for this and the following steps is the spherical coordinates. In this system, the imaging volume may be subdivided into voxels with location $(r_1, \theta_1, \phi_1)$ and size $(\Delta r_1, \Delta\theta_1, \Delta\phi_1)$ (see FIG. 2A). A voxel is a volumetric element that represents a value on a three dimensional grid. In some examples, the cone surface 400 may not cover a uniform thickness; however, the cone surface 400 covers a uniform polar angle $\Delta\theta_1$.

2) For each cone surface 400, a system matrix is constructed. The system matrix A={$a_{ij}$} has $n_d \times n_p$ elements, where i=1 . . . $n_d$, j=1 . . . $n_p$, and $n_d$ equals a number of absorbing detector pixels multiplied by an absorbing detector energy bin, $n_p$=number of voxels to be imaged. In order to obtain the spectra detected by the individual absorbing detector pixels, the imaging voxels and the absorbing detector pixels are further divided into subvoxels and subpixels. For example, the imaging voxels are divided into 8×8×8=512 and the subvoxels are divided into 8×8=64 subpixels. Each subvoxel and subpixel is small enough; therefore, their properties are regarded as uniform values. The photons 324 from the scatter detector 220 travel and intercept one of the subvoxels and the Compton scattering profile is calculated with the Klein-Nishina formula. After scattering, the scattered photons 328 travel and are detected by one of the subpixels in the absorbing detector 230, thus providing both the detection coordinates and energy information. Combining all the calculations of the subpixels within one pixel corresponding to one particular voxel, the energy response of that pixel for the scattered photons 328 from that voxel may be calculated. The energy information is then binned to give entries in the system matrix. Because each voxel only scatters a small solid angle of imaging photons 328 and each pixel only detects a small solid angle of scattered photons 328, the spectrum distribution may be relatively narrow and most elements in the system matrix corresponding to the photon energy may be zero, usually resulting in a sparse matrix.

3) After the system matrices for all the cone surfaces 400 are calculated, various statistical iterative imaging reconstruction algorithms may be carried out using standard procedures, such as Maximum-Likelihood Expectation-Maximization (ML-EM) and Penalized Likelihood with One-Step Late (OSL) procedure.

4) The reconstruction produces the scattering frequency map, which is proportional to the electron density if the imaging photons 324 are not attenuated. The photons scattered 326 by the scattering detector 220 are not used in the reconstruction process, but may provide other information. However, in some examples, the imaging photons 324 are attenuated and therefore need to be corrected. In CCVI device 200, the attenuation process is the Compton scattering itself, which is used to take an image of the object 300. Therefore, a solution to the coupled nonlinear equation for Compton attenuation and electron density may be determined by using a simple gradient descent algorithm, which in some instances is slow. This process is different than the PET approach for handling attenuation. In PET image reconstruction, the attenuation data are measured or estimated separately. (Note that the other attenuation processes, like photoelectric effect may have no effect as the coincident detection process excludes these photoelectric events.)

5) After the reconstruction in spherical coordinates, the output images are interpolated to generate a Cartesian coordinate image, which specifies each point in the object 300 by three numbers.

FIG. 6A shows a slice of a spherical phantom 600a (numerically simulated). The phantom is made of an aluminum (electron density 7.83 $10^{23}$ cm$^{-3}$) shell and water core. The diameter of the aluminum shell is 2 cm and the diameter of the water core is 1 cm. The scale bar shows the electron density in units of water electron density (3.33 $10^{23}$ cm$^{-3}$). The phantom center is placed on the x-axis and 2 cm away the origin (position of the scatter detector 220, see FIG. 2A). The slice is at z=0 on x-y plane. This slice corresponds to $\theta_1 = \pi/2$. FIG. 6B shows a reconstructed Compton scattering frequency map or image 600b of the slice after the OSL procedure described above. In some examples, it takes about 40 iterations to fail to observe changes. However, FIG. 6B is taken after 200 iterations. The values are scaled to be closer to the relative electron density. Since the lower part receives fewer total photons 324 due to the attenuation by the upper part, the outer-ring is non-uniform. The irregular edges arise from converting polar to Cartesian coordinates. FIG. 6C shows the reconstruction of a simple spherical phantom 600c of an aluminum shell with a water core after attenuation correction.

Figure 7A:
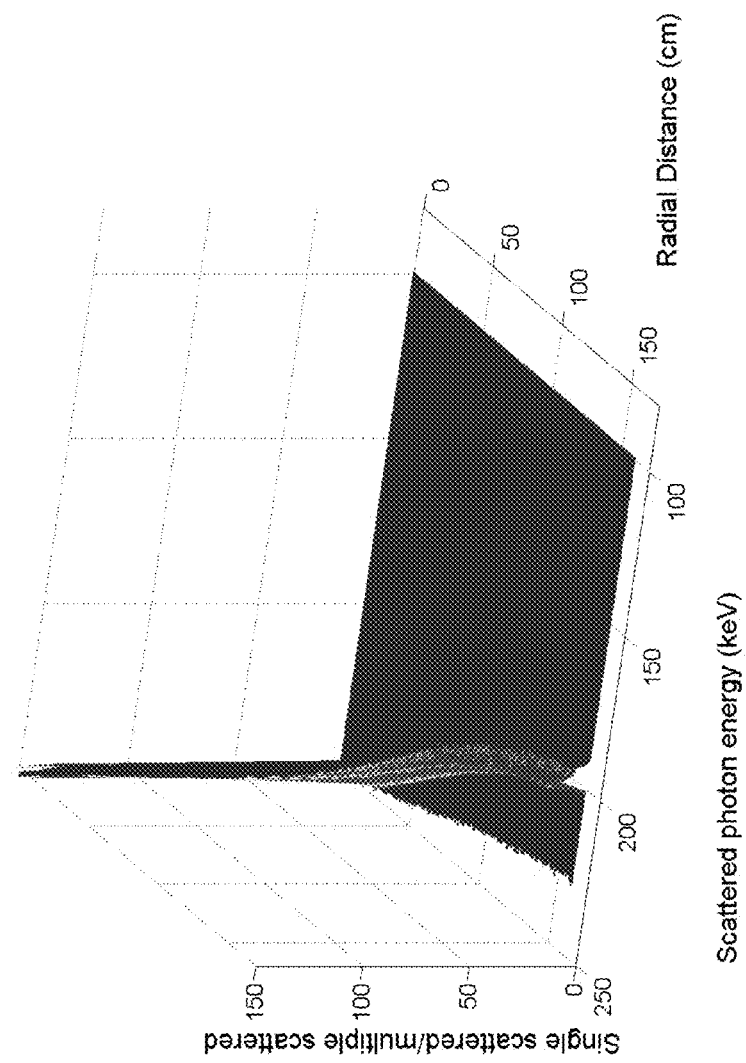
FIG. 7A is an exemplary graphical representation of a ratio of a single to multiple scattered photons for a cone angle of 0 rad.
Figure 7B:
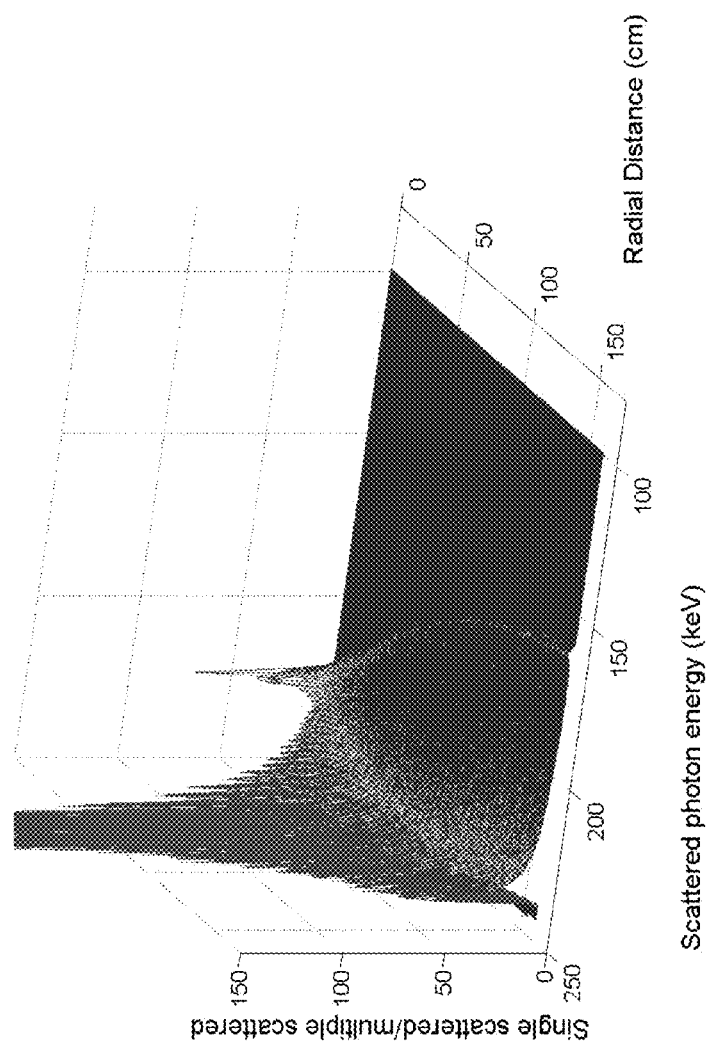
FIG. 7B is an exemplary graphical representation of a ratio of a single to multiple scattered photons for a cone angle of 0.6 rad.
Figure 7C:
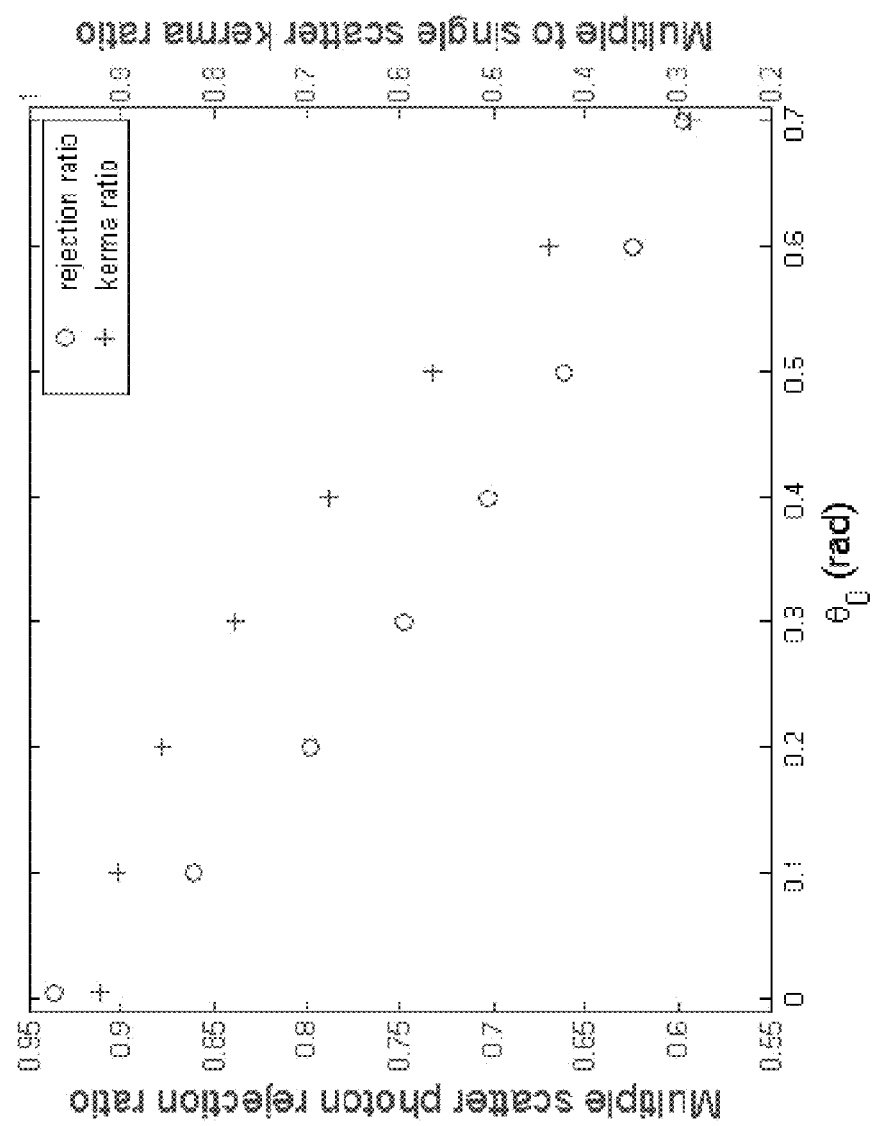
FIG. 7C is an exemplary graphical representation of multiple scatter photon rejection ratios as a function of cone angle, and multiple to single scatter kerma ratio.

Referring to FIG. 7A, with the setup of FIG. 3A, a ratio of a single to multiple scattered photon 328 detected at different radial locations and different scattered photon energies at cone angle $\theta_0$=0 rad is shown. In this instance, the single scattered photons 328 are concentrated in a narrow band of high ratio. The percentage of multiple scattered photons 328 in this band may be 6%, other values may also be available. Therefore, by only considering energies transferred, an exclusion of 94% of the multiple scattered photons 328 has occurred. As the cone angle $\theta_0$ increases, the single scattered photons 328 gradually spread out. FIG. 7B shows a similar plot to FIG. 7A.; however, $\theta_0$=0.6 rad instead of $\theta_0$=0 rad as shown in FIG. 7A (i.e., an increase in the cone angle). Thus, the ability of the CCVI device 200 to reject multiple scattering photons decreases as the cone and $\theta_0$ increase. FIG. 7C shows a plot of the rejection ration (left axis) versus the cone angle $\theta_0$. As shown, at the largest angle simulated (e.g., $\theta_0$=0.7 rad), the majority of multiple scattered photons 328 are still rejected. Also shown in FIG. 7C is the ratio of kerma induced by the multiple scattering photons 328 to that by single scattering photons 328. The average of this ratio over all directions intersecting the sphere is 0.56, which indicates that the dose induced by multiple scattering photons 328 is only slightly larger than that by single scattering photons 211. This information is used to estimate the extra dose induced by the multiple scattering photons 328, which we must discard after their detections.

Figure 8:
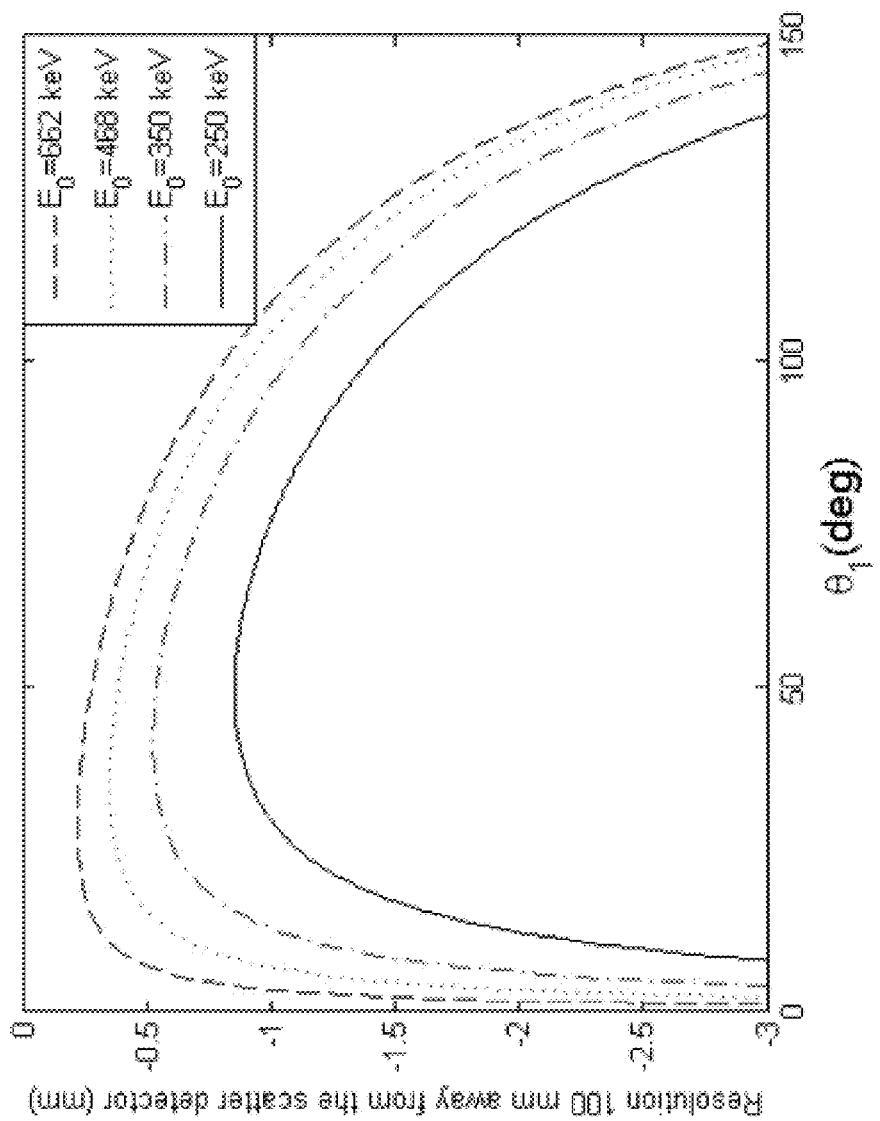
FIG. 8 is an exemplary graphical representation of a spatial resolution due to the energy resolution of the scatter detector, considering the electronic noise FWHM equals 0.5 keV.

Referring to FIG. 8, in some implementations, the resolution of the CCVI device 200 is limited from the pixelation of the absorbing detectors 230 and by the energy resolution of the scatter detector 220 and absorbing detectors 230. Considering the scatter detectors 220, the energy resolution of the absorbing detector 220 is normally characterized by its full width at half maximum (FWHM). FWHM refers to the difference between two extreme values of an independent variable of which a dependent variable equals to half of its maximum value. Therefore, the angular resolution $\Delta\theta_1$ may be obtained from Eq. 4 as:

$$\Delta\theta_1 = \frac{d\theta_1}{dE_1} \cdot FWHM \qquad (6)$$

The spatial resolution $\Delta r$ depends on the distance from the scatter detector 220, $$\Delta r = \Delta\theta_1 \cdot r \qquad (7)$$
$$= -m_e \left( \frac{1}{E_0} + \frac{1 - \cos(\theta_1)}{m_e} \right)^2 \cdot \csc(\theta_1) \cdot FWHM \cdot r$$

There are two main factors that contribute to FWHM: the Fano noise of the scatter detector 220 (which depends on the detected photon energy) and the electronic noise in the detector electronics (which is independent of the detected photon energy). FIG. 8 shows the detector resolution in the scatter detector 100 mm distant from the detector 220, 203. The energies $E_0$ of the incoming photons 322 are 662, 468, 350 and 250 keV. The electron noise FWHM is assumed to be 0.5 keV. The FWHM is a function of energy and scattering angle $\theta_1$ of the scatter detector 220.

Eq. 7 indicates that the spatial resolution worsens as the imaging point moves further from the scattering point. If a higher resolution is needed for the imaging point, the point may be positioned close to the scatter detector 220. In addition, by keeping other factors constant, the spatial resolution improves as the incoming photon energy is increased. However, high-energy photons 322 may increase the risk of radiation damage to the scatter detector 220 and decrease the quantum efficiency of the absorbing detector 230.

Doppler broadening is the broadening of spectral lines due to the Doppler Effect (i.e., the change in the frequency of a wave for an observer moving relative to its source) due to a distribution of velocities of atoms or molecules. In some implementations, the Doppler Effect arises from the momentum distribution of the electrons that scatter photons 322, and may impose a limit on the CCVI resolution (even if the detectors 220, 230 have perfect resolution). However, the Doppler broadening is significant only at low energies and large scattering angles. Therefore, photon energies $E_0$ used are sufficiently high to avoid the Doppler broadening effect; but the photon energies $E_0$ are below the damage threshold of the detectors 220, 230.

In some implementations, if the azimuthal angle $\phi_1$ (FIG. 2A) is limited to a narrow range by a linear collimator, for instance, around $\phi_1=0$ rad, the scattering location in the object 300 can be directly determined without reconstruction methods. This however limits the view to a slice of the object 300, producing a tomogram. To obtain a three dimensional volumetric image, several images are taken at different locations along the y-axis. An image can be directly obtained similar to the image shown in FIG. 6B. In this example, the only reconstruction to be considered is attenuation correction. Since this method combines Compton coincident scattering and tomogram images, we will refer to it as Compton coincident tomography (CCT).

The image dose for CCT may be estimated since imaging each individual voxel is almost independent of the other. The process is almost independent, but not completely independent, because a voxel in front of another voxel along a path of the imaging photon 324 may attenuate the imaging photon flux (number of photons in a time interval). In some examples, to get an estimate of the dose to be administered to a patient 300, the attenuation of the photons may be ignored. When using an x-ray emitting photons 322 of hundreds of keV (having a threshold value below 250 keV to avoid damaging the detector 220) for a higher resolution image, the attenuation of an object 300 having a size of a patient's body 300 is small. The dose may be estimated on one voxel to get the order of magnitude of the average dose on the object 300. In some examples, the voxel size is 2×2×2 $mm^3$ that is similar to a normal CT voxel. To achieve a relative electron density resolution of 5%, the absorbing detector 230 needs to detect about 400 photons 328 to scatter off this voxel. Assuming that 10% of the total scattered photons 328 are detected by the absorbing detector 230, then the remaining 90% loss may be due to factors like limited coverage of the absorbing detector 230, limited quantum efficiency of the absorbing detector 230, multiple scattering and other stray events, which must be rejected, and a few other minor factors. Therefore, the total scattered photon number is about 4000 to achieve the required 400 photons scattered off the voxel. The average Compton recoil electron energy may be calculated and is about 60 keV for 250 keV imaging photon. Therefore, the total recoil electron energy $E_e$ within the voxel is $3.9 \times 10^{-11}$ J.

In some examples, if the voxel is made of water, the kerma is calculated and equates to about 4.9 μGy. Kerma is a measure of the initial kinetic energies of the charged particles released by the impacting photons 322 in a unit mass of matter, usually measured in Joules/kilograms or the unit Gray (Gy). The actual absorbed dose is smaller than the calculated kerma. However, the kerma and the actual absorbed dose are close enough that the kerma can be used as a measurement to estimate the actual absorbed dose; the estimate is about a few thousand times less than a typical clinical CT dose.

In some examples, when the azimuthal angle $\phi$ is not limited to a narrow range and the CCVI device 200 creates three dimensional images using the CCVI device 200, the dose estimation is not as simple as the estimation described with respect to the CCT. In this case, an increase in dose is expected for similar parameters as a CCT image. In some examples, for a typical imaging size on the order of 100 voxels, the dose may increase 100 times. Even with this increase, the dose administered to the patient 300 is still less than the current dose being administered for CT imaging. With TOF detection, the imaging dose of CCVI device 200 can be reduced in a manner similar to TOF-PET. The rate reduction depends on the time resolution of the TOF detection.

Figure 9:
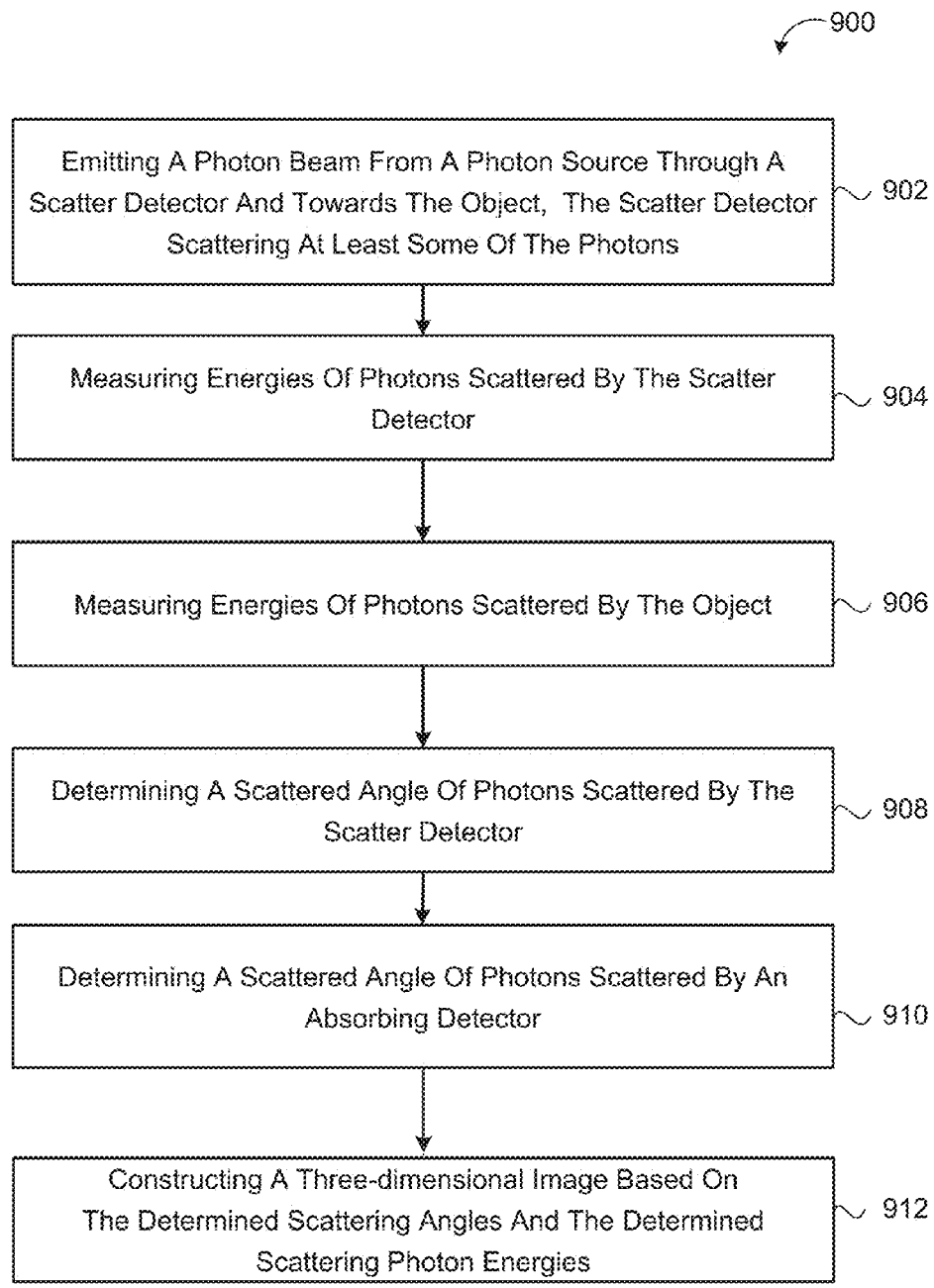
FIG. 9 is a schematic view of an exemplary arrangement of operations for operating an exemplary Compton coincident volumetric imaging device.

FIG. 9 provides an exemplary arrangement 900 of operations for a method of volumetric imaging of an object 300. The method 900 includes emitting 902 a photon beam 320 from a photon source 210 through a scatter detector 220 and towards an object 300. The scatter detector 220 scatters at least some of the photons 322 when they collide with electrons 304. The method 900 further includes measuring 904 energies of photons 324, 326 scattered by the scatter detector 220, and measuring 906 energies of photons 328 scattered by the object 300. The method 700 further includes determining 708 a scattered angle $\theta_1$ of photons 324 scattered by the scatter detector 220, and determining 910 a scattered angle $\theta_2$ of photons scattered by an absorbing detector or an object 300. Additionally, the method 900 includes constructing 912 a three-dimensional image based on the determined scattering angles $\theta_1$, $\theta_2$ and the determined scattering photon energies $E_1$, $E_2$.

Figure 10:
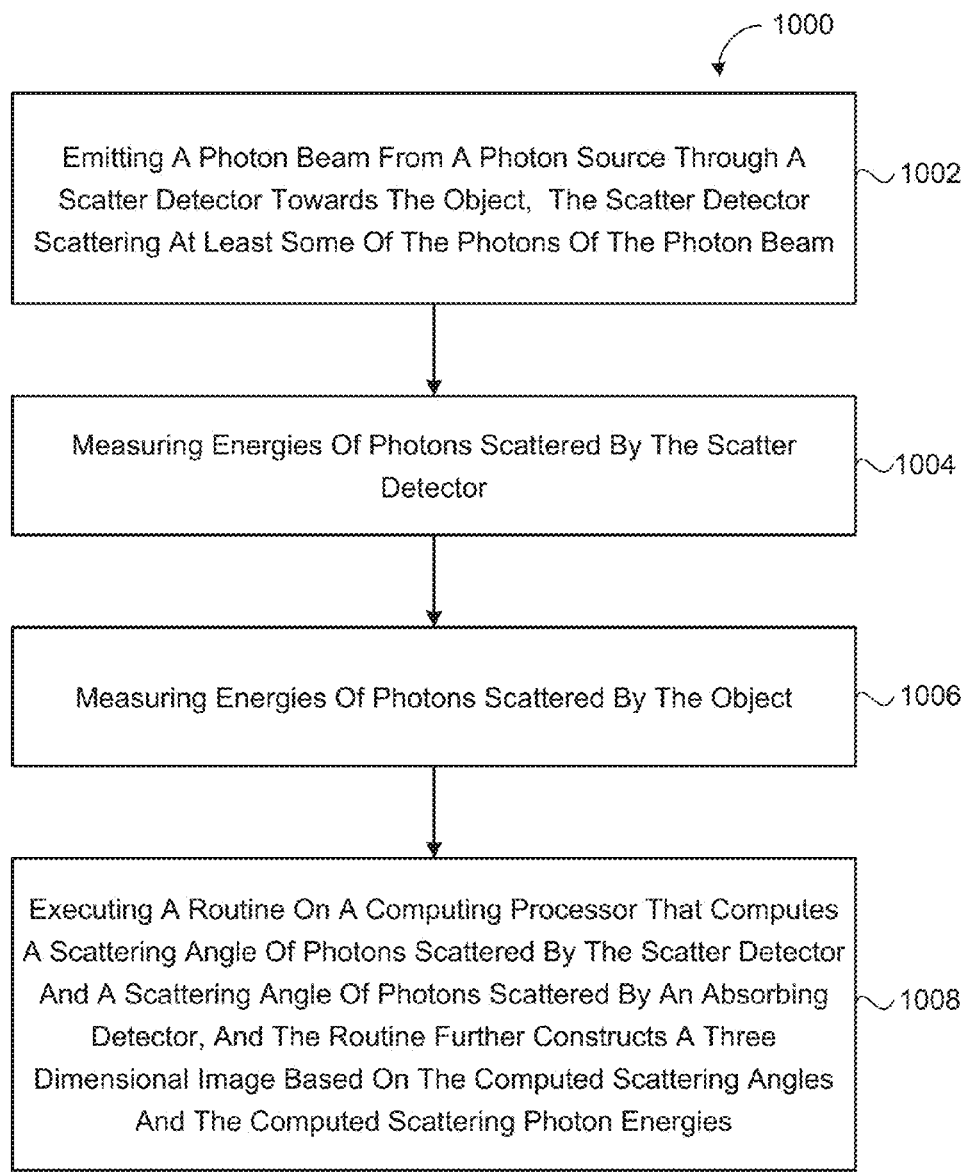
FIG. 10 is a schematic view of an exemplary arrangement of operations for operating an exemplary Compton coincident volumetric imaging device.

FIG. 10 provides an exemplary arrangement of operations for a method 1000 of volumetric imaging of an object 300. The method 1000 includes emitting 1002 a photon beam 320 of photons 322 from a photon source 210 through a scatter detector 220. The scatter detector 220 scatters at least some of photons 322 when they collide with electrons 304. The method 1000 further includes measuring 1004 energies of photons 324 scattered by the scatter detector 220 and measuring 1006 energies of photons 328 scattered by the object 300. The method 1000 also includes executing 1008 a routine on a computing processor that computes a scattering angle $\theta_1$ of photons 324 scattered by the scatter detector 220 and a scattering angle $\theta_2$ of photons 328 scattered by an absorbing detector 230 or an object 300, the routine further constructs a three dimensional image based on the computed scattering angles $\theta_1$, $\theta_2$ and the computed scattering photon energies $E_1$, $E_2$.

In some examples, the method 900, 1000 includes determining the scattered angle and the scattering energy of a photon 324, 326, 328 scattered by the scatter and absorbing detectors 220, 230 occurring simultaneously. Determining the scattering energy $E_1$ of a photon scattered by the scatter detector 220 includes calculating equation 1 previously described. In some examples, the method 900, 1000 further includes determining an electron density of the object 300. The method 900, 1000 may include performing calculations based on equations 1-4 to determine the scattering photon angle $\theta_1$, and a scattering location $\vec{r}_1$ from the scatter detector 220 to the object 300.

Various implementations of the systems and techniques described here can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

A number of implementations have been described. Nevertheless, it will be understood that various modifications may be made without departing from the spirit and scope of the disclosure. Accordingly, other implementations are within the scope of the following claims.

What is claimed is:

1. A volumetric imaging device for constructing a three dimensional image of an object, the volumetric imaging device comprising:
   a source comprising:
      an x-ray or gamma ray source for emitting photons; and
      a scatter detector arranged between the object and the photon source, wherein the photon source emits photons towards the scatter detector, the scatter detector scattering at least some of the photons and detecting the photons scattered from the scatter detector, the object scattering at least some of the scattered photons from the scatter detector;
   an absorbing detector arranged to detect scattered photons from the object; and
   an image constructor for constructing the three dimensional image based on the scattered photons from the scatter detector and the scattered photons from the object.

2. The volumetric imaging device of claim 1, wherein the image constructor calculates an electron density of the object.

3. The volumetric imaging device of claim 1, wherein the scatter and the absorbing detectors detect a photon simultaneously.

4. The volumetric imaging device of claim 1, wherein the scatter detector has a thickness of about 1 mm.

5. The volumetric imaging device of claim 1, wherein the source further comprises an electron detector positioned adjacent to the scatter detector.

6. The volumetric imaging device of claim 1, wherein the photon source is a synchrotron radiation source.

7. The volumetric imaging device of claim 1, wherein the photon source is an X-Ray tube with a monochromator.

8. The volumetric imaging device of claim 1, wherein the detectors are static with respect to one another.

9. The volumetric imaging device of claim 1, wherein the photon source is a radioisotope.

10. The volumetric imaging device of claim 9, wherein the radioisotope is Cesium-137 with a photon energy of 662 keV.

11. The volumetric imaging device of claim 1, wherein the scatter detector measures a first recoil energy $E_e$ being an energy of electrons.

12. The volumetric imaging device of claim 11, wherein a scattered photon energy $E_1$ is determined from the following equation:

$$E_1 = E_0 - E_e$$

where $E_0$ is a photon energy of the photons from the photon source.

13. The volumetric imaging device of claim 12, wherein a scattering photon angle $\theta_1$ is determined from the following equation:

$$\frac{1}{E_1} = \frac{1}{E_0} + \frac{1}{m_e}(1 - \cos(\theta_1))$$

where $m_e$ is the electron mass and equals 511 keV.

14. The volumetric imaging device of claim 13, wherein a position $\vec{r}_1$ from the scatter detector to the object is determined according to the following equation:

$$\frac{\vec{r_1} \cdot (\vec{r_2} - \vec{r_1})}{|\vec{r_1}||\vec{r_2} - \vec{r_1}|} = \cos(\theta_2)$$

where $\vec{r}_2$ is the absorbing detector pixel position, and $\theta_2$ is a scattering photon angle at the object.

15. The volumetric imaging device of claim 1, wherein a time-of-flight is determined by recording the arrival time of the detected photons at the scatter detector and the absorbing detector.

16. The volumetric imaging device of claim 1, further comprising an electron detector positioned behind the scatter detector for detecting escaped electrons from the scatter detector.

17. The volumetric imaging device of claim 1, wherein the photon source emits a photon beam having a threshold value of 250 keV.

18. The volumetric imaging device of claim 1, wherein the image constructor receives location information of the photons scattered by the object based on a location determined by $(\vec{r}_2, \theta_1, \theta_2)$ in a spherical coordinate system, wherein $\vec{r}_2$ is the absorbing detector pixel positions, $\theta_1$ is a scattering photon angle at the scatter detector and $\theta_2$ is a scattering photon angle at the object.

19. A volumetric imaging device for capturing an image of an object, the volumetric imaging device comprising:
   an x-ray or gamma ray source that emits a beam of photons;
   a scatter detector positioned between the object and the photon source, the scatter detector scatters at least some of the photons emitted by the photon source, the scatter detector detects the scattered photons from the scatter detector, wherein the scattered photons from the scatter detector impact the object and are further scattered by the object; and
   an absorbing detector arranged to detect the photons scattered by the scatter detector and the photons scattered by the object, the scatter and absorbing detectors simultaneously detecting a photon.

20. The volumetric imaging device of claim 19, wherein the scatter detector has a thickness of about 1 mm.

21. The volumetric imaging device of claim 19, wherein the photon source includes an electron detector positioned adjacent to the scatter detector.

22. The volumetric imaging device of claim 19, wherein the photon source is a synchrotron radiation source.

23. The volumetric imaging device of claim 19, wherein the photon source is an X-Ray tube with a monochromator.

24. The volumetric imaging device of claim 19, wherein the detectors are static with respect to one another.

25. The volumetric imaging device of claim 19, wherein the photon source is a radioisotope.

26. The volumetric imaging device of claim 25, wherein the radioisotope is Cesium-137 with a photon energy of 662 keV.

27. The volumetric imaging device of claim 19, wherein the scatter detector measures a first recoil energy $E_e$ being an energy of electron.

28. The volumetric imaging device of claim 27, wherein a scattered photon energy $E_1$ is determined from the following equation:

$$E_1 = E_0 - E_e$$

where $E_0$ is a photon energy of the photons from the photon source.

29. The volumetric imaging device of claim 28, wherein a scattering photon angle $\theta_0$ is determined from the following equation:

$$\frac{1}{E_1} = \frac{1}{E_0} + \frac{1}{m_e}(1 - \cos(\theta_1))$$

where $m_e$ is the electron mass and equals 511 keV.

30. The volumetric imaging device of claim 29, wherein a radius $\vec{r}_1$ from the scatter detector to the object is determined according to the following equation:

$$\frac{\vec{r}_1 \cdot (\vec{r}_2 - \vec{r}_1)}{|\vec{r}_1||\vec{r}_2 - \vec{r}_1|} = \cos(\theta_2)$$

where $\vec{r}_2$ is the absorbing detector pixel position, and $\theta_1$ is a scattering photon angle at the object.

31. The volumetric imaging device of claim 19, wherein a time-of-flight is determined by recording the arrival time of the detected photons at the scatter detector and the absorbing detector.

32. The volumetric imaging device of claim 19, further comprising an electron detector positioned behind the scatter detector for detecting escaped electrons from the scatter detector.

33. The volumetric imaging device of claim 20, wherein the photon source emits a photon beam having a threshold value of 250 keV.

34. The volumetric imaging device of claim 19, wherein the image constructor receives location information of the photons scattered by the object based on a location determined by $(\vec{r}_2, \theta_1, \theta 2)$ in a spherical coordinate system, wherein $\vec{r}_2$ is the absorbing detector pixel positions, $\theta_1$ is a scattering photon angle at the scatter detector and $\theta_2$ is a scattering photon angle at the object.

35. A method of volumetric imaging of an object, the method comprising:
   emitting a photon beam from an x-ray or gamma ray source emitting photons through a scatter detector and towards the object, the scatter detector scattering at least some of the photons;
   measuring energies of photons scattered by the scatter detector;
   measuring energies of photons scattered by the object;
   determining a scattered angle of photons scattered by the scatter detector;
   determining a scattered angle of photons scattered by an absorbing detector; and
   constructing a three-dimensional image based on the determined scattering angles and the determined scattering photon energies.

36. The method of claim 35, wherein determining the scattered angles and the scattering energies of a photon scattered by both the scatter and absorbing detectors occurs simultaneously.

37. The method of claim 35, wherein determining the scattering energy $E_1$ of a photon scattered by the scatter detector includes calculating the following equation:

$$E_1 = E_0 - E_e$$

where $E_0$ is the photon energy of the photons from the photon beam, and $E_e$ is a recoil energy of electrons.

38. The method of claim 37, wherein the scattering photon angle $\theta_1$ is determined from the following equation:

$$\frac{1}{E_1} = \frac{1}{E_0} + \frac{1}{m_e}(1 - \cos(\theta_1))$$

where $m_e$ is the electron mass and equals 511 keV.

39. The method of claim 38, further comprising determining a radius $\vec{r}_1$ from the scatter detector to the object according to the following equation:

$$\frac{\vec{r}_1 \cdot (\vec{r}_2 - \vec{r}_1)}{|\vec{r}_1||\vec{r}_2 - \vec{r}_1|} = \cos(\theta_2)$$

where $\vec{r}_2$ is the absorbing detector pixel position, and $\theta_2$ is a scattering photon angle at the object.

40. The method of claim 35, wherein the method further includes determining an electron density of the object.

41. A method of volumetric imaging of an object, the method comprising:
   emitting a photon beam from an x-ray or gamma ray source for emitting photons through a scatter detector towards the object, the scatter detector scattering at least some of the photons of the photon beam;
   measuring energies of photons scattered by the scatter detector;
   measuring energies of photons scattered by the object; and
   executing a routine on a computing processor that computes a scattering angle of photons scattered by the scatter detector and a scattering angle of photons scattered by an absorbing detector, and the routine further constructs a three dimensional image based on the computed scattering angles and the computed scattering photon energies.

42. The method of claim 41, wherein computing the scattering angle and the scattering energy of photon scattered by the scatter and absorbing detectors occurs simultaneously.

43. The method of claim 41, wherein determining the scattering energy $E_1$ of a photon scattered by the scatter detector includes calculating the following equation:

$$E_1 = E_0 - E_e$$

where $E_0$ is the photon energy of the photons from the photon beam, and $E_e$ is a recoil energy of electrons.

44. The method of claim 43, wherein the scattering photon angle $\theta_1$ is determined from the following equation:

$$\frac{1}{E_1} = \frac{1}{E_0} + \frac{1}{m_e}(1 - \cos(\theta_1))$$

where $m_e$ is the electron mass and equals 511 keV.

45. The method of claim 44, further comprising determining a radius $\vec{r}_1$ from the scatter detector to the object according to the following equation:

$$\frac{\vec{r}_1 \cdot (\vec{r}_2 - \vec{r}_1)}{|\vec{r}_1||\vec{r}_2 - \vec{r}_1|} = \cos(\theta_2)$$

where $\vec{r}_2$ is the absorbing detector pixel position, and $\theta_2$ is a scattering photon angle at the object.

46. The method of claim 41, wherein the method further includes determining an electron density of the object.

* * * * *